(12) United States Patent
Mahoney et al.

(10) Patent No.: US 6,656,158 B2
(45) Date of Patent: Dec. 2, 2003

(54) DISPENSER FOR PATIENT INFUSION DEVICE

(75) Inventors: Derek Dwayne Mahoney, Manalapan, NJ (US); John T. Garibotto, Charlestown, MA (US); Kerry Dennis O'Mara, Lambertville, NJ (US); Christopher Carter Gregory, Newtown, PA (US); John Michael Margicin, Langhorne, PA (US); J. Christopher Flaherty, Topsfield, MA (US)

(73) Assignee: Insulet Corporation, Beverly, MA (US)

( * ) Notice: Subject to any disclaimer, the term of this patent is extended or adjusted under 35 U.S.C. 154(b) by 2 days.

(21) Appl. No.: 10/128,203

(22) Filed: Apr. 23, 2002

(65) Prior Publication Data

US 2003/0199824 A1 Oct. 23, 2003

(51) Int. Cl.[7] .............................................. A61M 37/00
(52) U.S. Cl. ........................................ 604/131; 604/151
(58) Field of Search ................................ 604/131, 132, 604/133, 134, 135, 151–155, 530, 531; 606/78, 105

(56) References Cited

U.S. PATENT DOCUMENTS

| 306,691 | A | 3/1884 | Arai |
|---|---|---|---|
| 303,013 | A | 8/1884 | Konopka |
| 315,727 | A | 3/1885 | Arai et al. |
| 311,735 | A | 10/1885 | Aran et al. |
| 405,524 | A | 2/1889 | Falk et al. |
| 3,631,847 | A | 1/1972 | Hobbs |
| 3,812,843 | A | 5/1974 | Wootten et al. |
| 3,885,662 | A | 5/1975 | Schaefer |
| 4,067,000 | A | 1/1978 | Carlson |
| 4,108,177 | A | 8/1978 | Pistor |
| 4,151,845 | A | 5/1979 | Clemens |
| 4,211,998 | A | 7/1980 | Junginger et al. |
| 4,231,019 | A | 10/1980 | Junginger et al. |
| 4,268,150 | A | 5/1981 | Chen |
| 4,364,385 | A | 12/1982 | Lossef |
| 4,373,527 | A | 2/1983 | Fischell |

(List continued on next page.)

FOREIGN PATENT DOCUMENTS

| DE | 4200595 | 7/1993 |
|---|---|---|
| DE | 19920896 | 9/2000 |
| EP | 0342947 | 5/1989 |

(List continued on next page.)

OTHER PUBLICATIONS

US 5,954,699, 9/1999, Jost et al. (withdrawn)
Web–Site Brochure dated Jan. 4, 2000. MiniMed 508. "Doing its job. Naturally." www.minimed.com/tiles/mm_113.htm.

(List continued on next page.)

Primary Examiner—Sharon Kennedy
(74) Attorney, Agent, or Firm—McDermott, Will & Emery

(57) ABSTRACT

A device for delivering fluid, such as insulin for example, to a patient. The device includes an exit port assembly, a syringe-like reservoir including a side wall extending towards an outlet connected to the exit port assembly. A threaded lead screw is received in the reservoir and a plunger has an outer periphery linearly slideable along the side wall of the reservoir and an inner periphery threadedly received on the lead screw. The plunger is non-rotatable with respect to the side wall such that rotating the lead screw causes the plunger to advance within the reservoir and force fluid through the outlet. The device also includes a dispenser having a return element for causes rotation of the lead screw, and a shape memory element. A changeable length of the shape memory element decreasing from an uncharged length to a charged length resets the return element.

135 Claims, 14 Drawing Sheets

U.S. PATENT DOCUMENTS

| | | |
|---|---|---|
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,498,843 A | 2/1985 | Schneider et al. |
| 4,507,115 A * | 3/1985 | Kambara et al. ............ 604/135 |
| 4,514,732 A | 4/1985 | Hayes, Jr. |
| 4,529,401 A | 7/1985 | Leslie et al. |
| 4,559,033 A | 12/1985 | Stephen et al. |
| 4,559,037 A | 12/1985 | Franetzki et al. |
| 4,560,979 A | 12/1985 | Rosskopk |
| 4,562,751 A | 1/1986 | Nason et al. |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,755,173 A | 7/1988 | Konopka et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,855,746 A | 8/1989 | Stacy |
| 4,882,600 A | 11/1989 | Van de Moere |
| 4,886,499 A | 12/1989 | Cirelli et al. |
| 4,898,579 A | 2/1990 | Groshong et al. |
| 4,969,874 A | 11/1990 | Michel et al. |
| 4,973,998 A | 11/1990 | Gates |
| 5,007,458 A | 4/1991 | Marcus et al. |
| 5,045,871 A | 9/1991 | Reinholdson |
| 5,062,841 A | 11/1991 | Siegel |
| 5,109,850 A | 5/1992 | Blanco et al. |
| 5,176,662 A | 1/1993 | Bartholomew et al. |
| 5,178,609 A * | 1/1993 | Ishikawa .................... 604/131 |
| 5,205,819 A | 4/1993 | Ross et al. |
| 5,213,483 A | 5/1993 | Flaherty et al. |
| 5,232,439 A | 8/1993 | Campbell et al. |
| 5,239,326 A | 8/1993 | Takai |
| 5,242,406 A | 9/1993 | Gross et al. |
| 5,244,463 A | 9/1993 | Cordner, Jr. et al. |
| 5,245,447 A | 9/1993 | Stemmle |
| 5,254,096 A | 10/1993 | Rondelet et al. |
| 5,257,980 A | 11/1993 | Van Antwerp et al. |
| 5,281,202 A | 1/1994 | Weber et al. |
| 5,312,337 A | 5/1994 | Flaherty et al. |
| 5,318,540 A | 6/1994 | Athayde et al. |
| 5,342,313 A | 8/1994 | Campbell et al. |
| 5,411,480 A | 5/1995 | Kriesel |
| 5,433,710 A | 7/1995 | Van Antwerp et al. |
| 5,452,033 A | 9/1995 | Balling et al. |
| 5,492,534 A | 2/1996 | Athayde et al. |
| 5,505,709 A | 4/1996 | Funderburk et al. |
| 5,507,288 A | 4/1996 | Bocker et al. .............. 128/633 |
| 5,514,096 A | 5/1996 | Hiejima |
| 5,533,389 A | 7/1996 | Kamen et al. |
| 5,545,152 A | 8/1996 | Funderburk et al. |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,660,728 A | 8/1997 | Saaski et al. |
| 5,665,065 A | 9/1997 | Colman et al. |
| 5,665,070 A | 9/1997 | McPhee |
| 5,695,490 A | 12/1997 | Flaherty et al. |
| 5,702,363 A | 12/1997 | Flaherty |
| 5,704,520 A | 1/1998 | Gross |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson |
| 5,800,405 A | 9/1998 | McPhee |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,991 A | 12/1998 | Gross et al. |
| 5,851,197 A | 12/1998 | Marano et al. |
| 5,858,005 A | 1/1999 | Kriesel |
| 5,875,393 A | 2/1999 | Altschul et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,931,814 A | 8/1999 | Alex et al. |
| 5,935,099 A | 8/1999 | Peterson et al. |
| 5,954,058 A | 9/1999 | Flaherty |
| 5,957,890 A | 9/1999 | Mann et al. |
| 5,965,848 A | 10/1999 | Altschul et al. |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,061,580 A | 5/2000 | Altschul et al. |
| 6,071,292 A | 6/2000 | Makower et al. |
| 6,144,847 A | 11/2000 | Altschul et al. |
| 6,152,898 A | 11/2000 | Olsen |
| 6,190,359 B1 * | 2/2001 | Heruth ....................... 604/131 |
| 6,363,609 B1 | 4/2002 | Pickren |
| 6,375,638 B2 * | 4/2002 | Nason et al. ................ 604/132 |
| 6,488,652 B1 * | 12/2002 | Weijand et al. .......... 604/93.01 |

FOREIGN PATENT DOCUMENTS

| | | |
|---|---|---|
| EP | 0763369 | 3/1997 |
| EP | 0867196 | 3/1998 |
| EP | 0937475 | 8/1999 |
| WO | WO81/01658 | 6/1981 |
| WO | WO86/06796 | 11/1986 |
| WO | WO98/00193 | 1/1998 |
| WO | WO98/01071 | 1/1998 |
| WO | WO00/19887 | 9/1999 |
| WO | WO99/62576 | 9/1999 |
| WO | WO99/56803 | 11/1999 |
| WO | WO0010628 | 3/2000 |
| WO | WO00/29047 | 5/2000 |
| WO | WO00/29049 | 5/2000 |
| WO | WO00/74752 | 5/2000 |
| WO | WO00/30705 | 6/2000 |
| WO | WO00/78210 | 6/2000 |
| WO | WO00/48112 | 8/2000 |
| WO | WO00/61215 | 10/2000 |
| WO | WO01/52727 | 1/2001 |
| WO | WO01/5663 | 8/2001 |
| WO | WO01/76684 | 10/2001 |

| | | |
|---|---|---|
| WO | WO02/20073 | 3/2002 |

OTHER PUBLICATIONS

Web–Site Brochure dated Dec. 20, 1999. Applied Medical Technology. "508 Pump Information". www.applied–medical.co.uk/508.htm.

Web–Site Brochure dated Jan. 1, 2000. "The Glucose Sensor". www.animascorp.com/sensor_f.html.

Web–Site Brochure dated Dec. 20, 1999. "The Animas R–1000 Insulin Pump". www.animascorp.com/pump_f_s.html.

Web–Site Brochure dated Dec. 20, 1999. "The Animas R–1000 Insulin Pump". www.animascorp.com/pump_f_f.html.

Web–Site Brochure dated Jan. 4, 2000. SOOIL–Homepage. "Portable Insulin Pump". www.sooil.com/intro2.htm.

Web–Site Brochure dated Jan. 4, 2000. SOOIL–Homepage. "Portable Insulin Pump". www.sooil.com/product2.htm.

Web–Site Brochure dated Jan. 4, 2000. SOOIL–Homepage. "Portable Insulin Pump". www.sooil.com/product3.htm.

Web–Site Brochure dated Jan. 1, 2000. SOOIL–Homepage. "Portable Insulin Pump". www.sooil.com/product4.htm.

* cited by examiner

DISPENSER FOR PATIENT INFUSION DEVICE

CROSS-REFERENCE TO RELATED APPLICATIONS

The present application is related to co-pending U.S. patent application Ser. No. 10/128,205, which was filed on the same day as the present application, is entitled DISPENSER FOR PATIENT INFUSION DEVICE, and is assigned to the assignee of the present application and incorporated herein by reference.

The present application is also related to co-pending U.S. patent application Ser. number 09/943,992, filed on Aug. 31, 2001, and entitled DEVICES, SYSTEMS AND METHODS FOR PATIENT INFUSION, which is assigned to the assignee of the present application and incorporated herein by reference.

FIELD OF THE INVENTION

The present invention relates generally to medical devices, systems and methods, and more particularly to small, low cost, portable infusion devices and methods that are useable to achieve precise, sophisticated, and programmable flow patterns for the delivery of therapeutic liquids such as insulin to a mammalian patient. Even more particularly, the present invention is directed to a dispenser for a fluid delivery device that utilizes a shape memory element.

BACKGROUND OF THE INVENTION

Today, there are numerous diseases and other physical ailments that are treated by various medicines including pharmaceuticals, nutritional formulas, biologically derived or active agents, hormonal and gene based material and other substances in both solid or liquid form. In the delivery of these medicines, it is often desirable to bypass the digestive system of a mammalian patient to avoid degradation of the active ingredients caused by the catalytic enzymes in the digestive tract and liver. Delivery of a medicine other than by way of the intestines is known as parenteral delivery. Parenteral delivery of various drugs in liquid form is often desired to enhance the effect of the substance being delivered, insuring that the unaltered medicine reaches its intended site at a significant concentration. Also, undesired side effects associated with other routes of delivery, such as systemic toxicity, can potentially be avoided.

Often, a medicine may only be available in a liquid form, or the liquid version may have desirable characteristics that cannot be achieved with solid or pill form. Delivery of liquid medicines may best be accomplished by infusing directly into the cardiovascular system via veins or arteries, into the subcutaneous tissue or directly into organs, tumors, cavities, bones or other site specific locations within the body.

Parenteral delivery of liquid medicines into the body is often accomplished by administering bolus injections using a needle and reservoir, or continuously by gravity driven dispensers or transdermal patch technologies. Bolus injections often imperfectly match the clinical needs of the patient, and usually require larger individual doses than are desired at the specific time they are given. Continuous delivery of medicine through gravity feed systems compromise the patient's mobility and lifestyle, and limit the therapy to simplistic flow rates and profiles. Transdermal patches have special requirements of the medicine being delivered, particularly as it relates to the molecular structure, and similar to gravity feed systems, the control of the drug administration is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. An example of a use of an ambulatory infusion pump is for the delivery of insulin for the treatment of diabetes mellitus. These pumps can deliver insulin on a continuous basal basis as well as a bolus basis as is disclosed in U.S. Pat. No. 4,498,843 to Schneider et al.

The ambulatory pumps often work with a reservoir to contain the liquid medicine, such as a cartridge, a syringe or an IV bag, and use electromechanical pumping or metering technology to deliver the medication to the patient via tubing from the infusion device to a needle that is inserted transcutaneously, or through the skin of the patient. The devices allow control and programming via electromechanical buttons or switches located on the housing of the device, and accessed by the patient or clinician. The devices include visual feedback via text or graphic screens, such as liquid crystal displays known as LCD's, and may include alert or warning lights and audio or vibration signals and alarms. The device can be worn in a harness or pocket or strapped to the body of the patient.

Currently available ambulatory infusion devices are expensive, difficult to program and prepare for infusion, and tend to be bulky, heavy and very fragile. Filling these devices can be difficult and require the patient to carry both the intended medication as well as filling accessories. The devices require specialized care, maintenance, and cleaning to assure proper functionality and safety for their intended long term use. Due to the high cost of existing devices, healthcare providers limit the patient populations approved to use the devices and therapies for which the devices can be used.

Clearly, therefore, there was a need for a programmable and adjustable infusion system that is precise and reliable and can offer clinicians and patients a small, low cost, light-weight, easy-to-use alternative for parenteral delivery of liquid medicines.

In response, the applicant of the present application provided a small, low cost, light-weight, easy-to-use device for delivering liquid medicines to a patient. The device, which is described in detail in co-pending U.S. application Ser. No. 09/943,992, filed on Aug. 31, 2001, includes an exit port, a dispenser for causing fluid from a reservoir to flow to the exit port, a local processor programmed to cause a flow of fluid to the exit port based on flow instructions from a separate, remote control device, and a wireless receiver connected to the local processor for receiving the flow instructions. To reduce the size, complexity and costs of the device, the device is provided with a housing that is free of user input components, such as a keypad, for providing flow instructions to the local processor.

What are still desired are new and improved components, such as dispensers and reservoirs, for a device for delivering fluid to a patient. Preferably, the components will be simple in design, and relatively compact, lightweight, easy to manufacture and inexpensive, such that the resulting fluid delivery device can be effective, yet inexpensive and disposable.

SUMMARY OF THE INVENTION

The present invention provides a device for delivering fluid, such as insulin for example, to a patient. The device includes an exit port assembly, a reservoir including a side wall extending towards an outlet connected to the exit port assembly, and a threaded lead screw received in the reservoir and extending towards the outlet of the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir, which in turn causes fluid within the reservoir to be dispensed to the exit port assembly.

The device also includes a dispenser having a gear secured to the lead screw, and a moveable pawl positioned for contacting teeth of the gear during reciprocating linear movement of the moveable pawl adjacent the gear in first and second opposing linear directions. The pawl and the teeth are shaped such that linear movement of the pawl past the gear in the first linear direction causes rotation of the gear in the first rotational direction, while linear movement of the pawl past the gear in the second linear direction causes no rotation of the gear.

The dispenser also includes an elongated shape memory element having a changeable length decreasing from an uncharged length to a charged length when at least one charge is applied to the shape memory element. The shape memory element is connected between the moveable pawl such that the changeable length of the shape memory element decreasing from an uncharged length to a charged length causes linear movement of the moveable pawl past the gear in one of the first and the second linear directions. The use of a shape memory element helps provide a dispenser that is simple in design, and relatively compact, lightweight, and easy to manufacture.

According to one aspect of the present invention, the shape memory element includes two-way shape memory material. According to another aspect, the shape memory element includes one-way shape memory material.

According to a further aspect, the shape memory element includes a first set of at least two elongated parallel portions. Thinner parallel portions are provided in place of a single thicker shape memory element to provide the same pulling force, but with a quicker actuation time.

The present invention provides another device for delivering fluid. The device includes an exit port assembly, a reservoir having a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir. The device also includes a gear secured to the lead screw and a moveable pawl assembly having a cage coaxially arranged with respect to the lead screw about the gear. The cage is linearly movable in opposing first and second linear directions.

A first pawl extends from the cage and is biased against teeth of the gear. The first pawl and the teeth are shaped and oriented such that the first pawl rotates the gear in the first rotational direction during linear movement of the cage in the first linear direction, but causes no rotation of the gear during linear movement of the cage in the second linear direction. In addition, the first pawl prevents rotation of the gear in an opposite second rotational direction.

A second pawl extends from the cage and is biased against the teeth of the gear. The second pawl and the teeth are shaped and oriented such that the second pawl rotates the gear in the first rotational direction during linear movement of the cage in the second linear direction, but causes no rotation of the gear during linear movement of the cage in the first linear direction. In addition, the second pawl prevents rotation of the gear in the opposite second rotational direction.

According to one exemplary embodiment, at least one elongated shape memory element is connected between the cage of the moveable pawl assembly and at least one member fixed with respect to the cage, such that a changeable length of the shape memory element decreasing from an uncharged length to a charged length causes linear movement of the moveable pawl assembly with respect to the gear.

According to one aspect of the present invention, the first and the second pawls are resiliently flexible. According to another aspect, the first and the second pawls have arcuate profiles. According to a further aspect, the first pawl and the second pawl are offset with respect to a tooth pitch of the gear. The moveable pawl assembly provides very small increments of plunger advancement without requiring additional elements, such as reducing gears connected between the plunger lead screw and the pawl assembly.

The present invention provides an additional device for delivering fluid. The device includes an exit port assembly, a reservoir including a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir. First and second gears are coaxially secured to the lead screw for rotation therewith. The device also includes a moveable pawl assembly including a cage movable in opposing first and second linear directions adjacent the gears. A first pawl extends from the cage and is biased against teeth of the first gear, and the first pawl and the teeth of the first gear are shaped and oriented such that the first pawl rotates the first gear in the first rotational direction during linear movement of the cage in the first linear direction, but causes no rotation of the first gear during linear movement of the cage in the second linear direction. In addition, the first pawl prevents rotation of the first gear in an opposite second rotational direction. A second pawl extends from the cage and biased against teeth of the second gear, and the second pawl and the teeth of the second gear are shaped and oriented such that the second pawl rotates the second gear in the first rotational direction during linear movement of the cage in the first linear direction, but causes no rotation of the second gear during linear movement of the cage in the second linear direction. In addition, the second pawl prevents rotation of the second gear in the opposite second rotational direction.

According to one aspect of the present invention, the first and the second pawls have the same length, and the first and the second gears are identical but are out of phase by a single tooth pitch. This arrangement provides very small increments of plunger advancement without requiring additional elements, such as reducing gears connected between the plunger lead screw and the pawl assembly.

The present invention provides a further device for delivering fluid. The device includes an exit port assembly, a reservoir including a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir. A gear is coaxially secured to the lead screw for rotation therewith, and the device further includes a moveable pawl assembly having a cam pivotally mounted coaxially on the lead screw adjacent the gear for pivotal movement in opposing first and second pivotal directions about the lead screw.

A first pawl is secured to the cam and extends towards the gear, and the first pawl and teeth of the gear are shaped and oriented such that the first pawl rotates the gear in the first rotational direction during pivotal movement of the cam in the first pivotal direction, but causes no rotation of the gear during pivotal movement of the cam in the second pivotal direction. A second pawl is secured to the cam and extends towards the teeth of the gear, wherein the second pawl and the teeth of the gear are shaped and oriented such that the second pawl rotates the gear in the first rotational direction during pivotal movement of the cam in the first pivotal direction, but causes no rotation of the gear during pivotal movement of the cam in the second pivotal direction. The first and second pawls have different lengths such that pivotal movement of the cam in the first pivotal direction can produce less than a tooth pitch of gear advancement.

The present invention provides yet another device for delivering fluid. The device includes an exit port assembly, a reservoir including a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir.

The device also includes a dispenser having a barrel cam coaxial secured to the lead screw for rotation therewith and including a continuous circumferential groove with helical segments having orientations extending in the first rotational direction and successively alternating between opposing first and second ends of the barrel cam. A slide is linearly movable in opposing first and second linear directions parallel with the lead screw and adjacent the gear. The slide includes a finger extending from the slide and into the circumferential groove of the barrel cam. When the finger extends into one of the helical segments, linear movement of the slide causes rotation of the barrel cam and the lead screw in the first rotational direction.

According to one aspect of the present invention, the groove of the barrel cam also includes axial segments extending axially from each of junctures between the successive helical segments towards the ends of the barrel cam. When the finger extends into one of the axial segments, linear movement of the slide causes no rotation of the barrel cam and the lead screw. The combination of helical and axial segments can be used to control the amount of rotational motion of the lead screw produced from the linear motion of the slide.

The present invention provides a further device for delivering fluid. The device includes an exit port assembly, a reservoir including a side wall extending towards an outlet connected to the exit port assembly, and a threaded lead screw received in the reservoir. A plunger is secured to the lead screw and has an outer periphery linearly slideable along the side wall of the reservoir. The plunger and the lead screw are operatively arranged such that rotation of the lead screw in a first direction causes the plunger to slide along the side wall towards the outlet of the reservoir.

The device further includes a dispenser having a crankshaft operatively connected to the lead screw such that rotation of the crankshaft in a first rotational direction of the crankshaft causes rotation of the lead screw in the first rotational direction of the lead screw. The crankshaft includes a main shaft rotatable about a longitudinal axis, at least one counter weight secured to the main shaft for rotation therewith, and at least one crank pin. The crank pin is secured to the main shaft through the counter weight and has a longitudinal axis parallel to but radially offset from the longitudinal axis of the main shaft.

At least one elongated shape memory element is connected between the crank pin and at least one member fixed with respect to the crankshaft such that the changeable length of the shape memory element decreasing from an uncharged length to a charged length causes rotation of the crankshaft.

The present invention, therefore, provides a device for delivering fluid to a patient including new and improved components, such as dispensers utilizing shape memory elements. The components are simple in design, and relatively compact, lightweight, easy to manufacture and inexpensive, such that the resulting fluid delivery device is also relatively compact, lightweight, easy to manufacture and inexpensive such that the device can be inexpensive and disposable. In particular, the new and improved components of the present invention advantageously use shape memory elements to reduce complexity and costs.

These aspects of the invention together with additional features and advantages thereof may best be understood by reference to the following detailed descriptions and examples taken in connection with the accompanying illustrated drawings.

BRIEF DESCRIPTION OF THE DRAWINGS

FIG. 7a is a perspective view of a shape memory element of the dispenser of FIGS. 6 and 7;

Like reference characters designate identical or corresponding components and units throughout the several views.

DETAILED DESCRIPTION OF EXEMPLARY EMBODIMENTS

Figure 2:
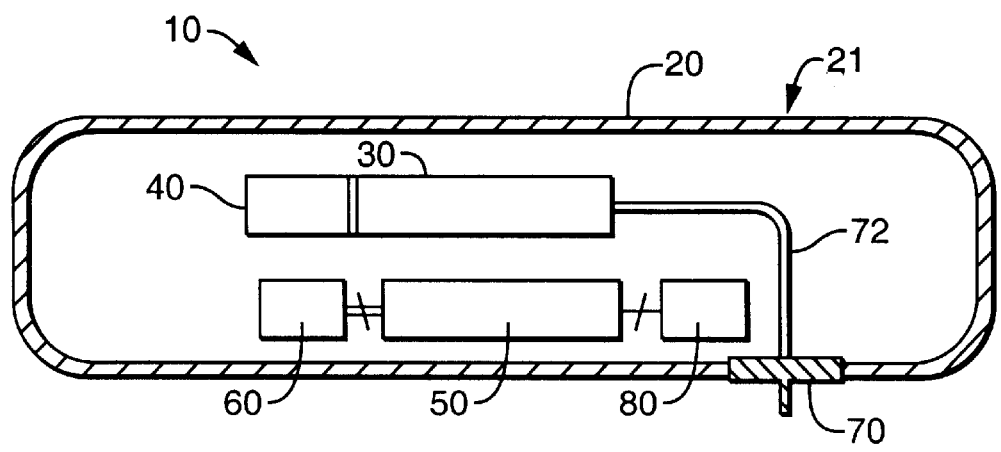
FIG. 2 is a sectional side view of the fluid delivery device of FIG. 1.

Referring first to FIG. 2, there is illustrated an exemplary embodiment of a fluid a delivery device 10 including a dispenser 40 constructed in accordance with the present invention. The dispenser 40 causes fluid flow between a reservoir 30 and an exit port assembly 70 during operation of the device 10. In general, shape memory elements are utilized in accordance with the present invention to provide effective, yet simple and inexpensive dispensers for fluid delivery devices.

The fluid delivery device 10 of FIG. 2 can be used for the delivery of fluids to a person or animal. The types of liquids that can be delivered by the fluid delivery device 10 include, but are not limited to, insulin, antibiotics, nutritional fluids, total parenteral nutrition or TPN, analgesics, morphine, hormones or hormonal drugs, gene therapy drugs, anticoagulants, analgesics, cardiovascular medications, AZT or chemotherapeutics. The types of medical conditions that the fluid delivery device 10 might be used to treat include, but are not limited to, diabetes, cardiovascular disease, pain, chronic pain, cancer, AIDS, neurological diseases, Alzheimer's Disease, ALS, Hepatitis, Parkinson's Disease or spasticity. In addition, it should be understood that the dispenser 40 according to the present invention can be used with fluid delivery devices other than those used for the delivery of fluids to persons or animals.

Figure 1:
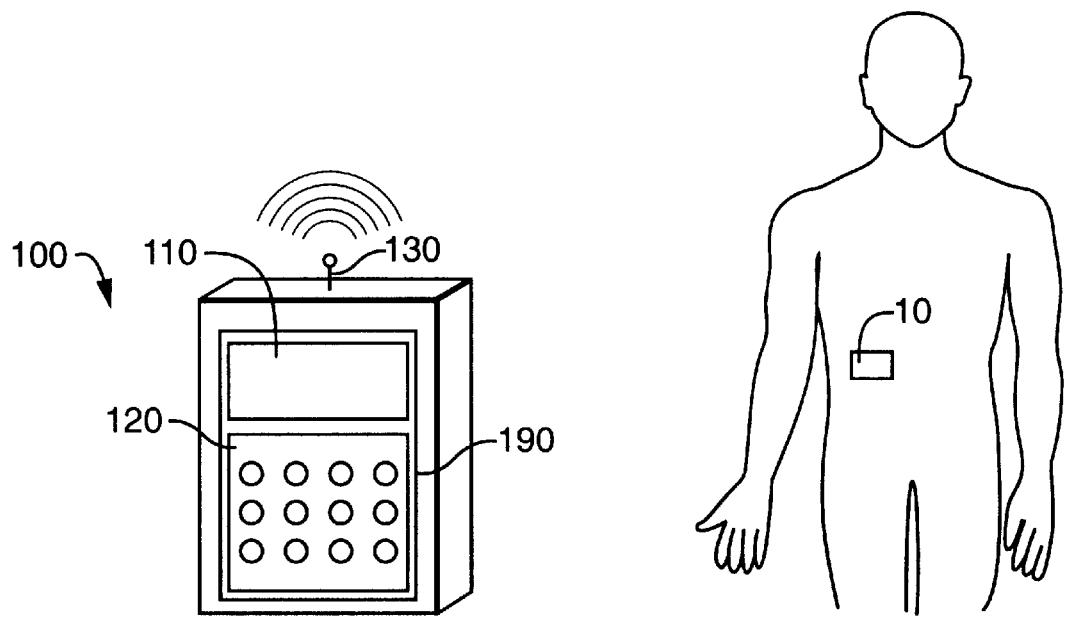
FIG. 1 is a perspective view of a first exemplary embodiment of a fluid delivery device constructed in accordance with the present invention and shown secured on a patient, and a remote control device for use with the fluid delivery device (the remote control device being enlarged with respect to the patient and the fluid delivery device for purposes of illustration)

The fluid delivery device 10 also includes a processor or electronic microcontroller (hereinafter referred to as the "local" processor) 50 connected to the dispenser 40. The local processor 50 is programmed to cause a flow of fluid to the exit port assembly 70 based on flow instructions from a separate, remote control device 100, an example of which is shown in FIG. 1. Referring also to FIG. 2, the fluid delivery device 10 further includes a wireless receiver 60 connected to the local processor 50 for receiving the flow instructions from the separate, remote control device 100 and delivering the flow instructions to the local processor. The device 10 also includes a housing 20 containing the exit port assembly 70, the reservoir 30, the dispenser 40, the local processor 50 and the wireless receiver 60.

As shown, the housing 20 of the fluid delivery device 10 is free of user input components for providing flow instructions to the local processor 50, such as electromechanical switches or buttons on an outer surface 21 of the housing, or interfaces otherwise accessible to a user to adjust the programmed flow rate through the local processor 50. The lack of user input components allows the size, complexity and costs of the device 10 to be substantially reduced so that the device 10 lends itself to being small and disposable in nature. Examples of such devices are disclosed in co-pending U.S. patent application Ser. No. 09/943,992, filed on Aug. 31, 2001, and entitled DEVICES, SYSTEMS AND METHODS FOR PATIENT INFUSION, which is assigned to the assignee of the present application and has previously been incorporated herein by reference.

In order to program, adjust the programming of, or otherwise communicate user inputs to the local processor 50, the fluid delivery device 10 includes the wireless communication element, or receiver 60 for receiving the user inputs from the separate, remote control device 100 of FIG. 1. Signals can be sent via a communication element (not shown) of the remote control device 100, which can include or be connected to an antenna 130, shown in FIG. 1 as being external to the device 100.

The remote control device 100 has user input components, including an array of electromechanical switches, such as the membrane keypad 120 shown. The control device 100 also includes user output components, including a visual display, such as a liquid crystal display (LCD) 110. Alternatively, the control device can be provided with a touch screen for both user input and output. Although not shown in FIG. 1, the remote control device 100 has its own processor (hereinafter referred to as the "remote" processor) connected to the membrane keypad 120 and the LCD 110. The remote processor receives the user inputs from the membrane keypad 120 and provides "flow" instructions for transmission to the fluid delivery device 10, and provides information to the LCD 110. Since the remote control device 100 also includes a visual display 110, the fluid delivery device 10 can be void of an information screen, further reducing the size, complexity and costs of the device 10.

The communication element 60 of the device 10 preferably receives electronic communication from the remote control device 100 using radio frequency or other wireless communication standards and protocols. In a preferred embodiment, the communication element 60 is a two-way communication element, including a receiver and a transmitter, for allowing the fluid delivery device 10 to send information back to the remote control device 100. In such an embodiment, the remote control device 100 also includes an integral communication element comprising a receiver and a transmitter, for allowing the remote control device 100 to receive the information sent by the fluid delivery device 10.

The local processor 50 of the device 10 contains all the computer programs and electronic circuitry needed to allow a user to program the desired flow patterns and adjust the program as necessary. Such circuitry can include one or more microprocessors, digital and analog integrated circuits, resistors, capacitors, transistors and other semiconductors and other electronic components known to those skilled in the art. The local processor 50 also includes programming, electronic circuitry and memory to properly activate the dispenser 40 at the needed time intervals.

In the exemplary embodiment of FIG. 2, the device 10 includes a power supply 80, such as a battery or capacitor, for supplying power to the local processor 50. The power supply 80 is preferably integrated into the fluid delivery device 10, but can be provided as replaceable, e.g., a replaceable battery.

Although not shown, the device 10 can include sensors or transducers such as a reservoir volume transducer or a reservoir pressure transducer, for transmitting information to the local processor 50 to indicate how and when to activate the dispenser 40, or to indicate other parameters determining flow, pump flow path prime condition, blockage in flow path, contact sensors, rotary motion or other motion indicators, as well as conditions such as the reservoir 30 being empty or leaking, or the dispensing of too much or too little fluid from the reservoir, etc.

The volume of the reservoir 30 is chosen to best suit the therapeutic application of the fluid delivery device 10 impacted by such factors as available concentrations of medicinal fluids to be delivered, acceptable times between refills or disposal of the fluid delivery device 10, size constraints and other factors. The reservoir 30 may be prefilled by the device manufacturer or a cooperating drug manufacturer, or may include external filling means, such as a fill port having needle insertion septum or a Luer connector, for example. In addition, the device 10 can be provided with a removable reservoir.

The exit port assembly 70 can include elements to penetrate the skin of the patient, such that the entire volume of the flow path 210 of the fluid delivery device 10 is predetermined. For example, a needle-connection tubing terminating in a skin penetrating cannula (not shown) can be provided as an integral part of the exit port assembly 70, with the skin penetrating cannula comprising a rigid member, such as a needle. The exit port assembly 70 can further be provided with injection means, such as a spring driven mechanism, to assist in penetrating the skin with the skin penetrating cannula. For example, if the cannula is a flexible tube, a rigid penetrator within the lumen of the tube can be driven through the skin by the injection means and then withdrawn, leaving the soft cannula in place in the subcutaneous tissue of the patient or other internal site. The injection means may be integral to the device 10, or removable soon after transcutaneous penetration.

Alternatively, the exit port assembly 70 can be adapted to connect, with a Luer connector for example, to a separate, standard infusion device that includes a skin penetrating cannula. In any event, the exit port assembly 70 can also be provided with a removable plug (not shown) for preventing leakage during storage and shipment if pre-filled, and during priming if filled by user, and prior to use. It should be understood that, as used herein, the term "flow path" is meant to include all portions of the fluid delivery device 10 that contain therapeutic fluid for delivery to a patient, e.g., all portions between the fill port of the reservoir to the tip of the needle of the exit port assembly.

Although not shown, the device 10 can also be provided with an adhesive layer on the outer surface of the housing 20 for securing the device 10 directly to the skin of a patient. The adhesive layer is preferably provided in a continuous ring encircling the exit port assembly 70 in order to provide a protective seal around the penetrated skin. The housing 20 can be made from flexible material, or can be provided with flexible hinged sections that allow the fluid delivery device 10 to flex during patient movement to prevent detachment and aid in patient comfort.

Referring to FIGS. 3 through 26b, the present disclosure provides various dispensers and/or reservoirs for use with the fluid delivery device 10 of FIGS. 1 and 2. The dispensers and the reservoirs are small and simple in design, and inexpensive and easy to manufacture, in order to further reduce the size, complexity and costs of the fluid delivery device 10, such that the device 10 continues to lend itself to being small and disposable in nature. In general, the device 10 is provided with non-pressurized reservoirs, and the dispensers are adapted to cause flow from the reservoirs. The dispensers are controlled by the local processor 50, which includes electronic programming, controls, and circuitry to allow sophisticated fluid delivery programming and control of the dispensers.

Figure 3:
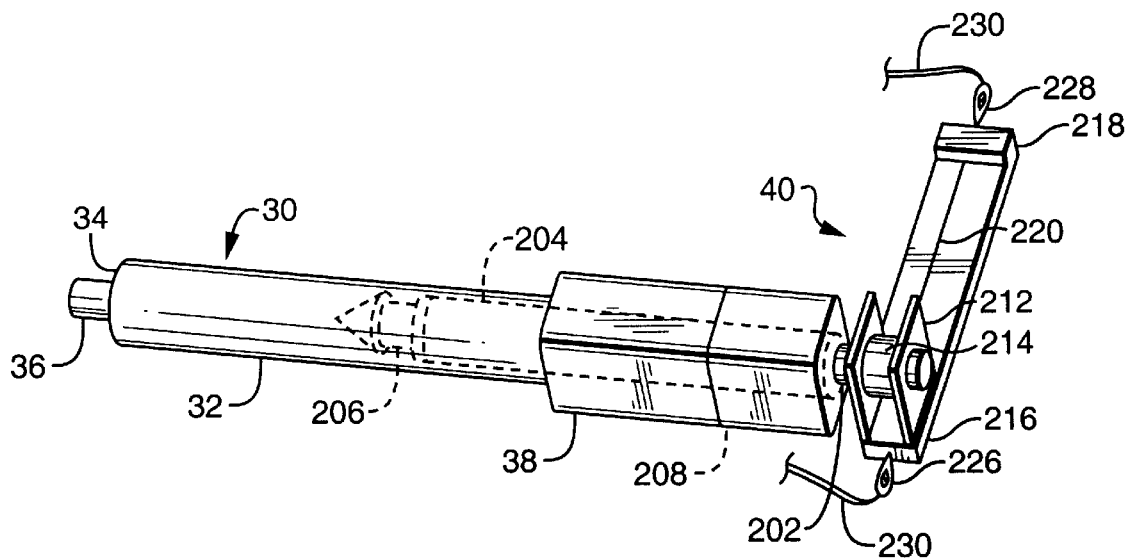
FIG. 3 is a perspective view of an exemplary embodiment of a reservoir, a plunger and a lead screw of the fluid delivery device of FIG. 1, and an exemplary embodiment of a dispenser constructed in accordance with the present invention for turning the lead screw.
Figure 4:
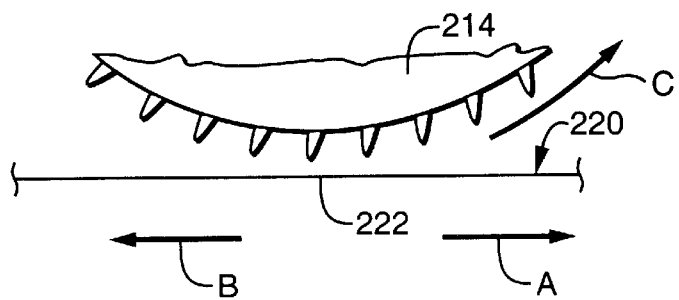
FIG. 4 is an enlarged perspective view of a gear and a shape memory element of the dispenser of FIG. 3.
Figure 5:
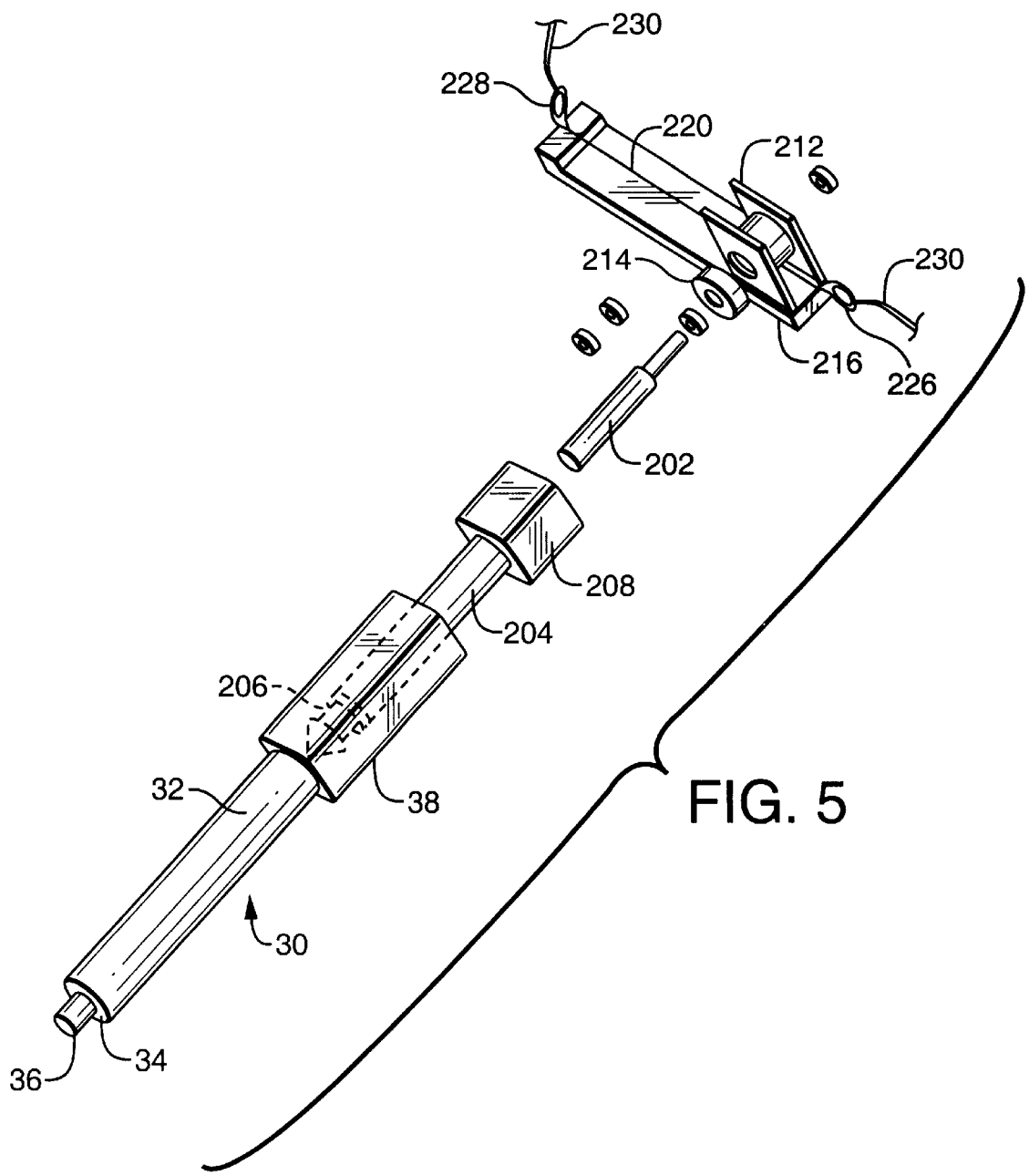
FIG. 5 is an exploded perspective view of the exemplary embodiments of the reservoir, the plunger, the lead screw and the dispenser of FIG. 3.

Referring first to the reservoir 30 and the dispenser 40 of FIGS. 3 through 5, in An addition to FIG. 2, the reservoir 30 is provided with a side wall 32 extending between an open end and an end wall 34 of the reservoir. The end wall 34 includes an outlet 36 for connection through a lumen 72 to the exit port assembly 70 of the device 10. The reservoir 30 also includes a threaded lead screw 202 mounted for rotation within the reservoir 30, and a plunger 204 threadedly received on the lead screw. The lead screw 202 is positioned coaxial with the side wall 32 and extends partly into the open end of the reservoir 30. The plunger 204 includes a tip 206 made of a resiliently flexible material, such as a silicone elastomer or rubber, that is shaped and sized to form a seal between the plunger 204 and the side wall 32 of the reservoir. Movement of the plunger 204 towards the end wall 34 of the reservoir 30, therefore, forces fluid through the outlet 36 to the exit port assembly 70.

The plunger 204 is prevented from rotating with respect to the side wall 32 so that, when the screw 202 is turned with respect to the plunger 204, the plunger is caused to move linearly along the screw 202 and within the reservoir 30. In the embodiment shown in FIG. 5, the reservoir 30 and the plunger 204 are provided with end portions 38, 208, respectively, having square cross-sections. Alternatively, the plunger 204 can be provided with at least one channel and the side wall 32 of the reservoir 30 can be provided with at least one protrusion extending along its length and received within the channel of the plunger (or vis versa) to prevent rotation of the plunger. In addition, the reservoir 30 and the plunger 204 can alternatively be provided with other matching non-circular cross-sections, such as oval, square or rectangular, along at least a portion of their length to prevent rotation of the plunger 204 with respect to the side wall 32, without the use of a protrusion and a channel. Such non-circular cross-sections can also include simply providing the side wall 32 and the plunger 204 with mating flat portions in otherwise circular cross-sections.

In order to reduce the cost of the reservoir 30, the lead screw 202 and the plunger 204 are preferably made from an inexpensive material. The lead screw 202 is made of a rigid material such as a metal, such as stainless steel, or a plastic, such as polyethylene or a polypropylene. The side wall 32 and the end wall 34 of the reservoir are preferably made from a rigid material such as a suitable metal (e.g., stainless steel) or plastic. The plunger 204 is relatively rigid and made of metal or plastic for engaging the threads of the lead screw 202. Since the device is preferably disposable, preventing thread wear between the lead screw 202 and the plunger 204 is not necessary, thereby allowing the use of less expensive materials and lower tolerances in the manufacture and assembly of the lead screw 202 and the plunger 204.

Figure 6:
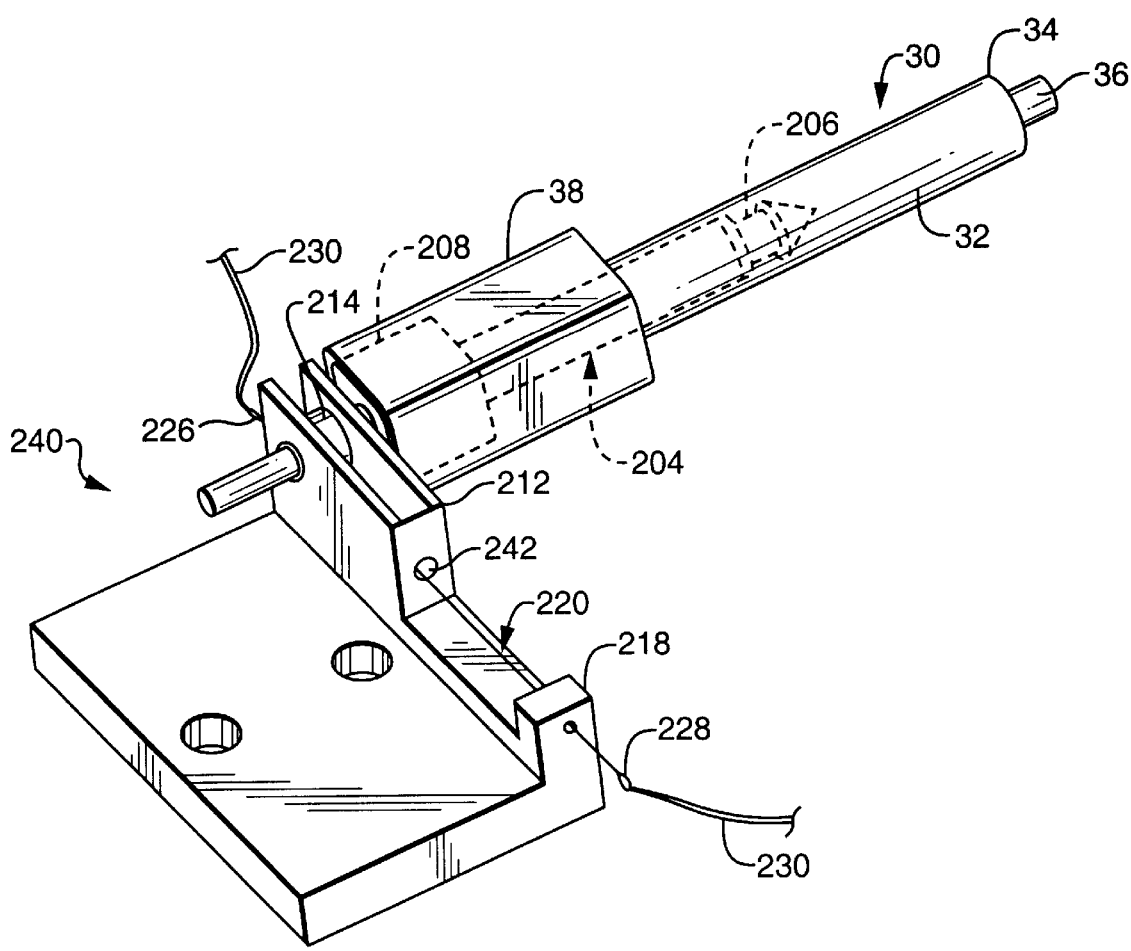
FIG. 6 is a perspective view of an exemplary embodiment of a reservoir, a plunger and a lead screw of the fluid delivery device of FIG. 1, and another exemplary embodiment of a dispenser constructed in accordance with the present invention for turning the lead screw.

Referring to FIGS. 3 through 5, the dispenser 40 causes fluid flow by turning the lead screw 202 of the reservoir 30. In the embodiment of FIGS. 3 and 6, the dispenser 40 includes a gear 214 coaxially fixed to the lead screw 202, such that rotation of the gear causes rotation of the lead screw. The gear 214 includes radially extending teeth (as shown best in FIG. 4). The lead screw 202 and the plunger 204 include screw threads that are shaped such that rotation of the lead screw 202 in a first direction, which is counter-clockwise as shown in FIG. 4, causes movement of the plunger 204 towards the end wall 34 of the reservoir 30 to force fluid through the outlet 36 to the exit port assembly 70. The gear 214 and the lead screw 202 are mounted for rotation on a fixed gear bracket 212, as shown in FIGS. 3 and 5. Although not shown, the dispenser 40 also includes a pawl mounted on the fixed gear bracket 212 and engaging the teeth of the gear 214 to prevent rotation of the gear 214 and the lead screw 202 in a second direction, which is clockwise as shown in FIG. 4.

The exemplary embodiment of the dispenser 40 of the present invention also includes a shape memory element 220 made of a shape memory material. The application of an electrical current to shape memory material heats the material and results in molecular and crystalline restructuring of the shape memory material. If the shape memory material is in the shape of an elongated wire, for example, as the shape memory element 220 preferably is, this restructuring causes a decrease in length. Nitinol, a well-known alloy of nickel and titanium, is an example of such a so-called shape memory material and is preferred for use as the shape memory element 220.

In general, when a shape memory alloy is in its martensitic form (i.e., low temperature state), it is easily deformed to a new shape. However, when the alloy is heated through its transformation temperatures, it reverts to its austenite form (ie., high temperature state) and recovers its previous shape with great force. The temperature (or the level of electrical charge) at which the alloy remembers its high temperature form can be adjusted by slight changes in alloy composition and through heat treatment. In the nickel-titanium alloys, for instance, austenite temperature can be changed from above 100° C. to below 100° C. The shape recovery process occurs over a range of just a few degrees and the start or finish of the transformation can be controlled to within a degree or two if necessary.

These unique alloys also show a superelastic behavior if deformed at a temperature which is slightly above their transformation temperatures. This effect is caused by the stress-induced formation of some martensite above its normal temperature. Because it has been formed above its normal temperature, the martensite reverts immediately to undeformed austenite as soon as the stress is removed. This process provides a very springy, "rubberlike" elasticity in these alloys. A one-way SME alloy can be deformed, then recover to retain permanently its original shape when heated to a certain temperature. A two-way alloy, however, holds its original shape at one temperature and takes on another shape at a different temperature. Two-way memory is unique in that the material "remembers" different high temperature and low temperature shapes.

The shape memory element 220 of the embodiment of the present invention shown in FIGS. 3 through 5 comprises a two-way shape memory alloy. As shown in FIGS. 3 and 5, a first end 226 of the shape memory element 220 is secured to a first fixed member 216, and a second end 228 of the shape memory element 220 is secured to a second fixed member 218. The dispenser 40 includes wires 230 connecting the opposite ends 226, 228 of the shape memory element 220 to the processor 50 of the fluid delivery device.

A moveable pawl 222 is secured to the elongated shape memory element for linear movement adjacent the gear 214. The moveable pawl 222 engages the teeth of the gear 214, and the moveable pawl and the teeth are shaped such that linear movement of the moveable pawl 222 in a first direction past the gear 214, as shown by arrow "A" in FIG. 4, causes rotation of the gear 214 in the first direction, which is counter-clockwise as shown in FIG. 4 and illustrated by arrow "C". The moveable pawl 222 and the teeth of the gear 214 are also shaped such that linear movement of the moveable pawl 222 in a second direction past the gear 214, as shown by arrow "B" in FIG. 4, causes no rotation of the gear 214 (i.e., the moveable pawl and the teeth are shaped to slide over each other as the moveable pawl 222 moves past the gear 214 in the second direction).

When a charge is applied to the two-way elongated shape memory element 220 through the wires 230, the length of the shape memory element 220 decreases from an uncharged length to a charged length. The shape memory element 220 is arranged such that the changeable length of the shape memory element 220 decreasing from an uncharged length to a charged length causes linear movement of the moveable pawl 222 in the second direction past the gear 214, and thus no advancement of the plunger 204.

When the charge is removed from the two-way elongated shape memory element 220, the length of the shape memory element 220 increases from the charged length to the uncharged length. The shape memory element 220 is arranged so that, when the shape memory element 220 increases from the charged length to the uncharged length, the moveable pawl 222 moves linearly in the first direction past the gear 214. The uncharged shape memory element 220, therefore, rotates the gear 214 and the lead screw 202 in the first direction (and advances the piston 204 in the reservoir 30 to dispense fluid to the exit port assembly 70. The increase in length occurs with a force that is sufficient to rotate the gear 214 and the lead screw 202 in the first direction to advance the plunger 204.

While the dispenser 40 and the reservoir 30 of FIGS. 3 through 5 are arranged such that removing an electrical charge from the shape memory element 220 causes advancement of the plunger 204, the dispenser and the reservoir can alternatively be arranged such that providing an electrical charge to the shape memory element 220 causes advancement of the plunger 204.

Although not shown, the processor 50 can include capacitors for storing a charge received from the power source 80. The fluid delivery device 10 is calibrated so that a single charge from the processor 50 causes the dispensing of a predetermine volume of fluid, called pulse volume (PV), from the reservoir 30. In this manner, a desired volume to be delivered by the fluid delivery device 10 is dispensed by the release of multiple charges over a predetermined period. PV's delivered by infusion devices are typically chosen to be small relative to what would be considered a clinically significant volume. For insulin applications at a concentration of one hundred units per microliter 100 units/ml), a PV of less than two microliters, and typically a half of a microliter, is appropriate. If the fluid delivery device 10 is programmed via the remote control device 100 to deliver two units an hour, the processor 50 will deliver forty charges an hour, or a charge every ninety seconds, to the shape memory element 220. Other drugs or concentrations may permit a much larger PV. Various flow rates are achieved by adjusting the time between charges. To give a fixed volume or bolus, multiple charges are given in rapid succession until the bolus volume is reached.

Figure 7:
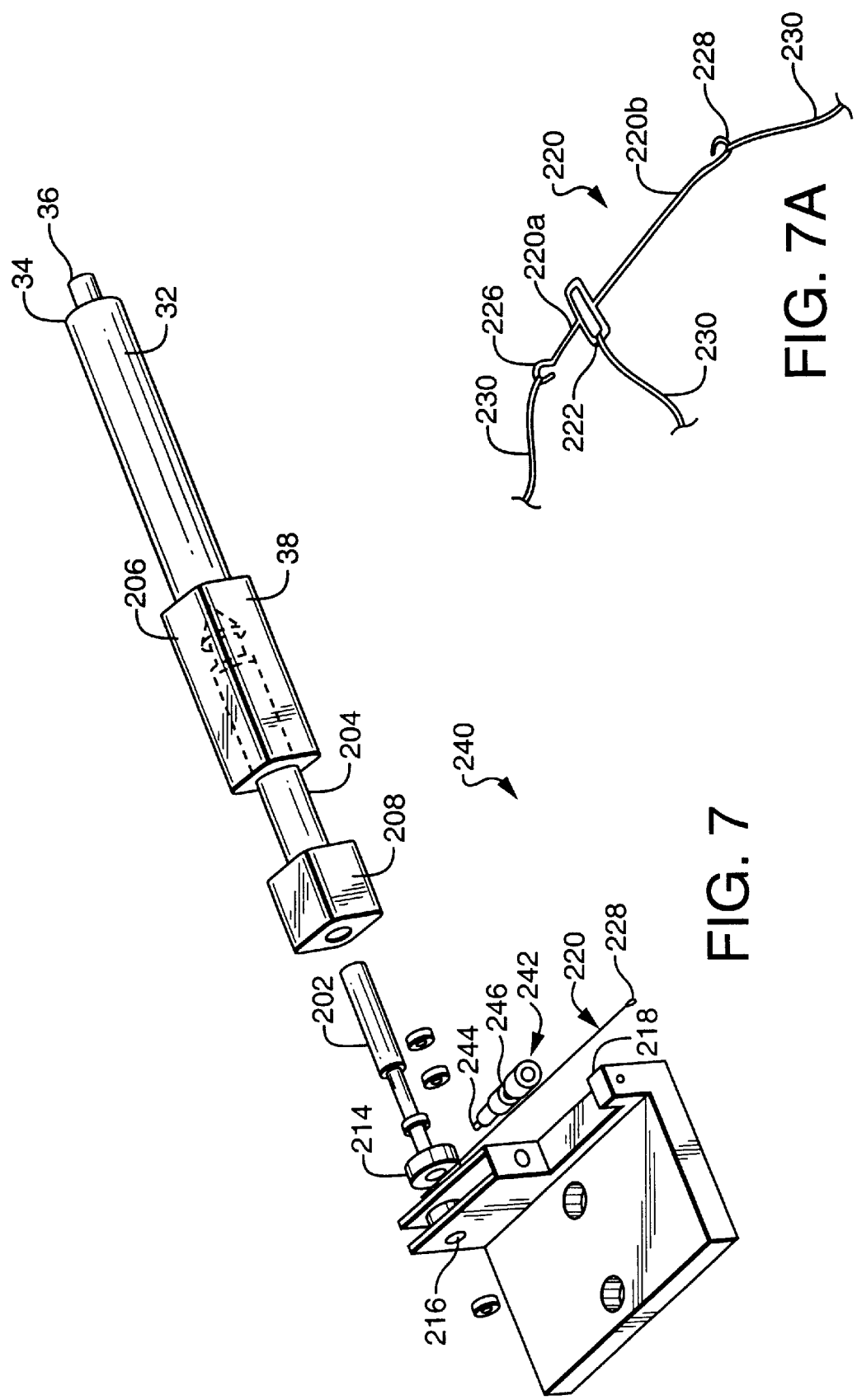
FIG. 7 is an exploded perspective view of the exemplary embodiments of the reservoir, the plunger, the lead screw and the dispenser of FIG. 6.
Figure 8:
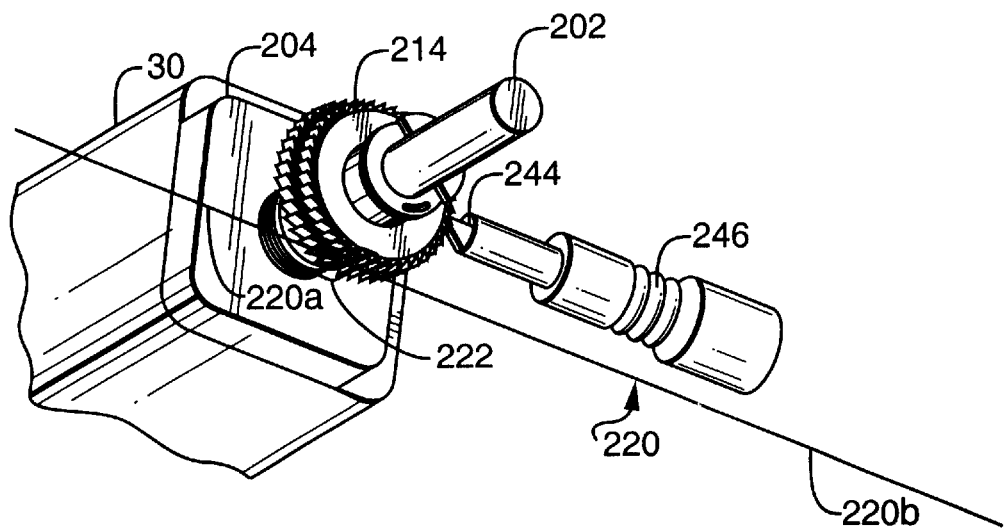
FIG. 8 is an enlarged perspective view of a portion of the exemplary embodiments of the reservoir, the plunger, the lead screw and the dispenser of FIG. 6.

Another exemplary embodiment of a dispenser 240 constructed in accordance with the present invention is shown in FIGS. 6 and 7. Elements of the dispenser 240 are similar to elements of the dispenser 40 of FIGS. 3 and 5 such that similar elements have the same reference numeral. In the embodiment 240 of FIGS. 6 and 7, however, the dispenser also includes a pawl assembly including a pawl biased against the gear by a spring. The pawl is shaped to allow rotation of the gear 214 in the first direction (which is counter-clockwise as shown in FIGS. 8, 9a and 9b) but prevent rotation of the gear in the second, opposite direction (which is clockwise as shown in FIGS. 8, 9a and 9b).

Referring also to FIG. 7a, the shape memory element 220 includes a first portion 220a extending between the first end 226 and the moveable pawl 222, and a second portion 220b extending between the moveable pawl 222 and the second end 228. A third electrical wire 230 is secured between the moveable pawl 222 and the processor (not shown in FIG. 7a) of the fluid delivery device, in addition to the electrical wires 230 connected between the processor and the ends 226, 228 of the shape memory element 220. In this manner, the first portion 220a and the second portion 220b can be independently charged.

Figure 9A:
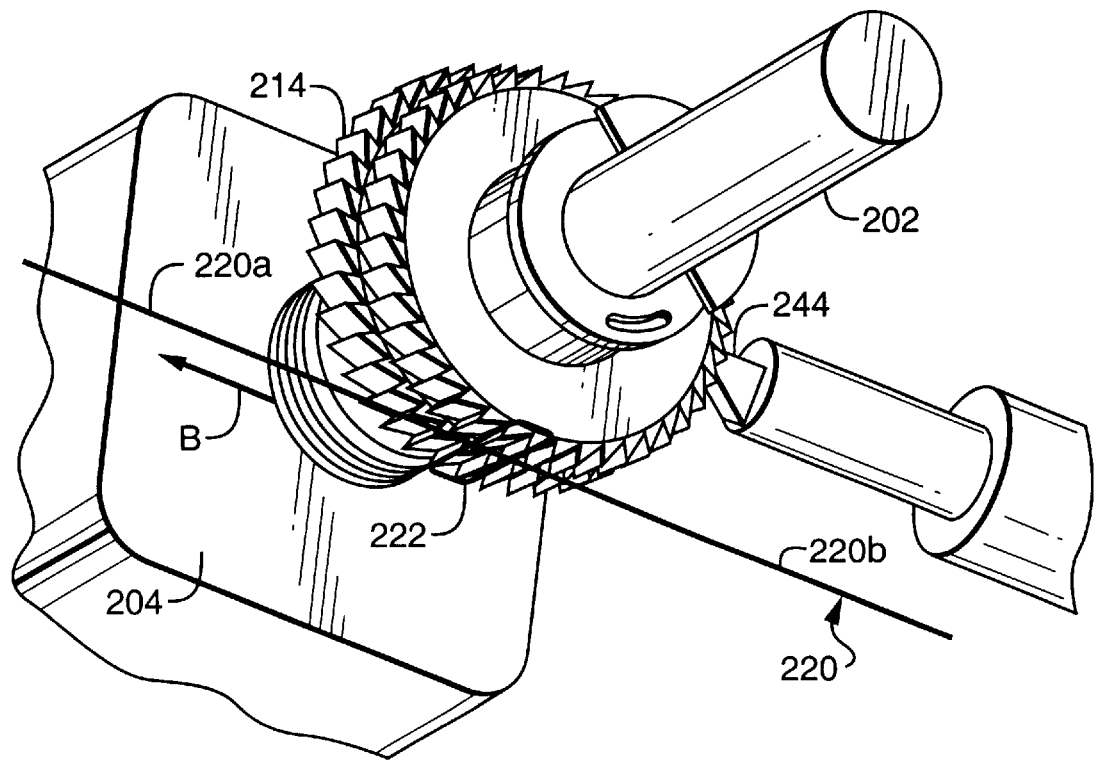
FIGS. 9a and 9b are further enlarged perspective views of a portion of the exemplary embodiments of the reservoir, the plunger, the lead screw and the dispenser of FIG. 6, illustrating operation of the dispenser.

During operation of the dispenser 240, removing a charge from the second portion 220b while applying a charge to the first portion 220a causes the moveable pawl 222 to move in the second direction past the gear 214, as illustrated by arrow "B" in FIG. 9a. The moveable pawl 222 and the teeth of the gear 214 are shaped such that linear movement of the moveable pawl 222 in the second direction past the gear 214 causes no rotation of the gear 214 (i.e., the moveable pawl and the teeth are shaped to slide over each other as the moveable pawl 222 moves past the gear 214 in the second direction).

Figure 9B:
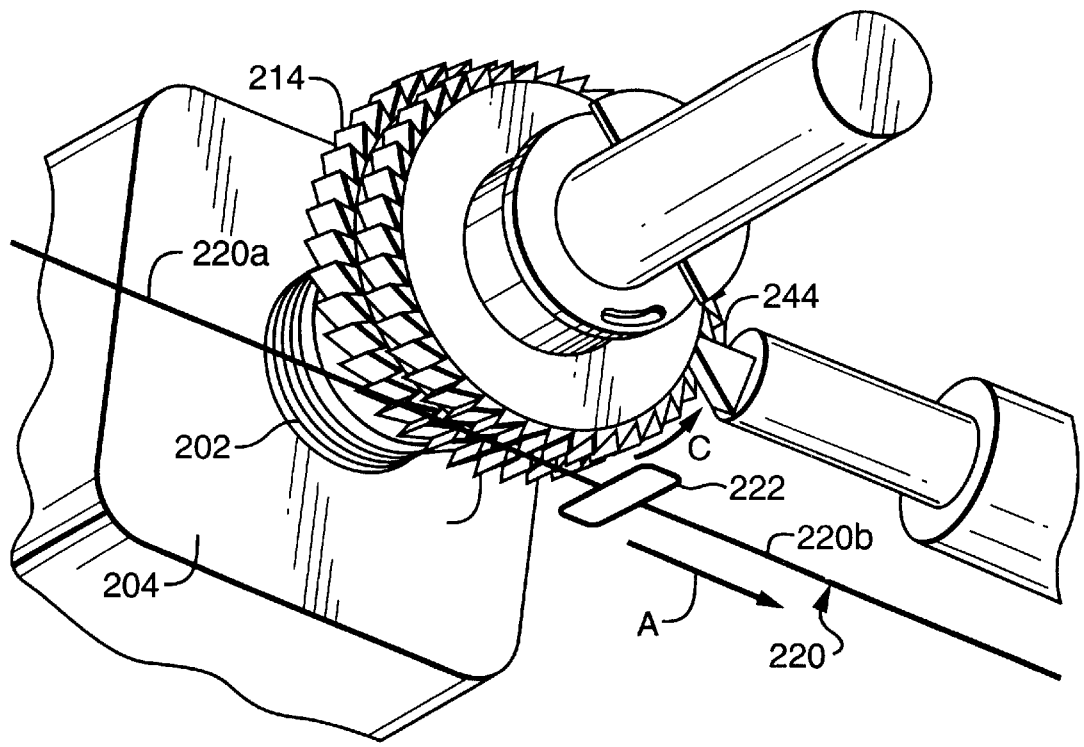

Then, removing the charge from the first portion 220a and applying a charge to the second portion 220b causes the moveable pawl 222 to move in the first direction past the gear 214, as illustrated by arrow "A" in FIG. 9b. The moveable pawl 222 and the teeth are shaped such that linear movement of the moveable pawl 222 in the first direction past the gear 214 causes rotation of the gear 214 in the first direction, which is counter-clockwise as shown in FIG. 9b and illustrated by arrow "C". The first portion 220a and the second portion 220b of the shaped memory element 220 are alternatively charged to cause reciprocating linear motion of the moveable pawl 222 and rotation of the gear 262 and the lead screw 202 in the first direction.

In the exemplary embodiment of the dispenser 240 of FIGS. 6 through 9, the shape memory element 220 and the moveable pawl 222 are constructed as a unitary piece from the same material. However, the moveable pawl 222 can be made as a separate piece and secured between the portions 220a, 220b of the shape memory element 220. In addition, the moveable pawl 222 can be made of a different material, such as an electrically non-conducting plastic for example.

In the exemplary embodiment of the dispenser 240 of FIGS. 6 through 9, the shape memory element 220 can be made from one of either a two-way or a one-way shape memory material. The type of shape memory material used can depend on the response time required of the dispenser 240. For example, if a faster cycle time is desired of the reciprocating shape memory element 220, two-way shape memory material is used.

Figure 10:
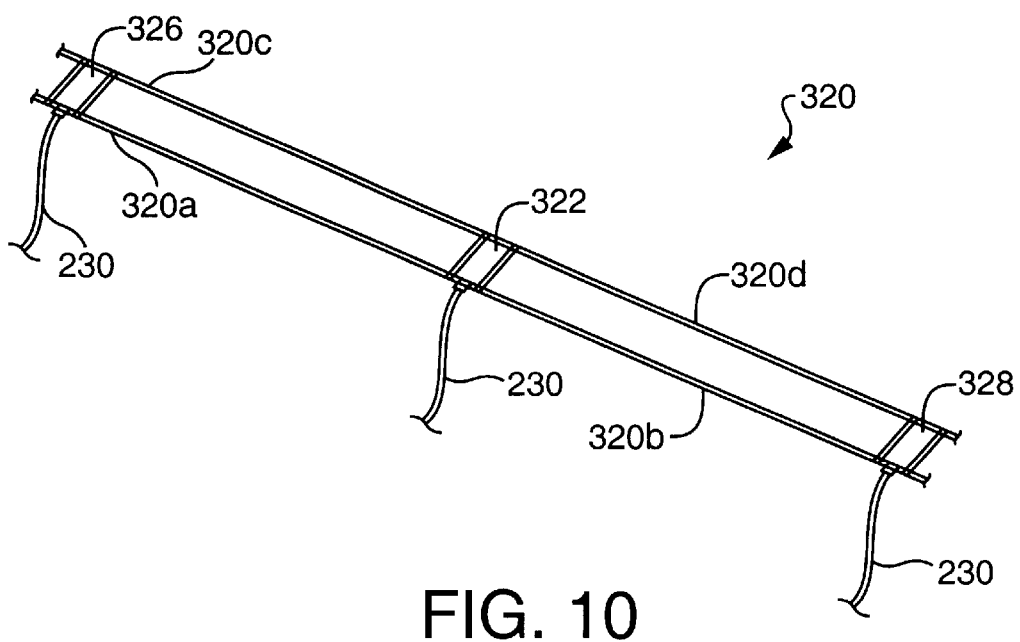
FIG. 10 is an enlarged perspective view of an alternative embodiment of a shape memory element constructed in accordance with the present invention for use with the dispenser of FIG. 6.

An alternative embodiment of a shape memory element 320 for use with the dispenser of FIGS. 6 through 9 is shown in FIG. 10. The shape memory element 320 is elongated and generally includes first and second opposing ends 326, 328 and a moveable pawl 322 for operatively interacting and rotating a gear. As shown, electrically wires 230 are connected to the ends 326, 328 and the moveable pawl 322 for connecting to the processor (not shown in FIG. 10) of the fluid delivery device. In order to increase the cycle time of the shape memory element 320 more than one parallel portions 320a, 320c are provided between the first end 326 and the moveable pawl 322 and more than one parallel portions 320b, 320d are provided between the moveable pawl 322 and the second end 328. The parallel portions 320a–320b of the shape memory element 320 are each made thinner than if single portions were used (e.g., the embodiment 220 of FIG. 9b) between the moveable pawl 322 and the ends 326, 328, since the thinner shape memory portions 320 react more quickly to heating and cooling. However, the parallel portions 320a–320b can create the same force as single portions.

TABLE I

Comparison of Different Sized Shape Memory Elements

| Cross-Sectional Diameter (inches) | Resistance (ohms/inch) | Maximum Pull Force (grams) | Off Time 90° C. Wire (seconds) |
|---|---|---|---|
| 0.0015 | 21.0 | 17 | 0.09 |
| 0.002 | 12.0 | 35 | 0.1 |
| 0.003 | 5.0 | 80 | 0.2 |
| 0.004 | 3.0 | 150 | 0.4 |
| 0.005 | 1.8 | 230 | 0.9 |
| 0.006 | 1.3 | 330 | 1.2 |
| 0.008 | 0.8 | 590 | 2.2 |
| 0.010 | 0.5 | 930 | 3.5 |
| 0.012 | 0.33 | 1250 | 6.0 |
| 0.015 | 0.2 | 2000 | 10.0 |

For example, Table I illustrates a comparison of pull forces and reaction times for different sized shape memory elements (i.e., SME wires having different cross-sectional diameters). Assuming the shape memory element has to provide about 300 grams of force to cause rotation of the gear and the lead screw, a single wire having a diameter of 0.006 inches can be used. However, 0.006 inch diameter shape memory wire has a reaction time of 1.2 seconds. Alternatively, two parallel 0.004 inch diameter shape memory wires can be used in place of the single 0.006 inch diameter shape memory wire to produce a force of about 300 grams, yet have quicker a reaction time of 0.4 seconds. Thus, the multiple, parallel shape memory portions 320a–320d are used to provide the same force in less time. In the exemplary embodiment of the shape memory element 320 of FIG. 10, the shape memory portions 320a–320d can be made from one of either a two-way or a one-way shape memory material, as desired.

An additional exemplary embodiment of a dispenser 340 constructed in accordance with the present invention is shown in FIGS. 11a through 11e. The dispenser 340 includes a gear 314 secured to the lead screw 202 and including radially extending teeth. The dispenser 340 also includes a moveable pawl assembly 342 including a cage 344 coaxially arranged with respect to the lead screw 202 about the gear 314. The cage 344 is linearly movable in opposing first and second linear directions, as illustrated respectively by arrows "A" and "B" in FIG. 11a.

The dispenser 340 of FIGS. 11a–11e advantageously provides the benefit of advancing the gear 314 by less than one tooth pitch for a cycle of linear movement of the cage 344. In this manner, secondary mechanisms, such as a gear 314 reduction train, are not necessary to provide the slow lead screw 202 rotational speeds that are desirable with the dispensing of some medications, such as insulin. The dispenser 340 also provides a very slow rotational speed to the lead screw 202 without requiring that the gear 314 be provided with very small teeth, which would increase the required tolerances of the gear 314 (and thus possibly increase the costs of the gear).

The dispenser 340 also includes a first pawl 346 extending from the cage 344 and biased against the teeth of the gear 314. The first pawl 346 and the teeth are shaped and oriented such that the first pawl 346 rotates the gear 314 in a first rotational direction, as illustrated by arrow "C" in FIG. 11a, during linear movement of the cage 344 in the first linear direction "A" but causes no rotation of the gear 314 during linear movement of the cage 344 in the second linear direction "B". In addition, the first pawl 346 and the gear teeth are shaped and oriented such that the first pawl prevents rotation of the gear 314 in an opposite, second rotational direction.

The dispenser 340 additionally includes a second pawl 348 extending from the cage 344 and biased against the teeth of the gear 314. The second pawl 348 and the teeth are shaped and oriented such that the second pawl 348 rotates the gear 314 in the first rotational direction "C" during linear movement of the cage 344 in the second linear direction "B" but causes no rotation of the gear 314 during linear movement of the cage 344 in the first linear direction "A". The second pawl 348 and the gear teeth are also shaped and oriented such that the second pawl prevents rotation of the gear 314 in the opposite, second rotational direction.

As shown in FIGS. 11a through 11e, the first and second pawls 346, 348 mirror each other. In particular, both of the pawls 346, 348 are the same size and have an elongated arcuate shape. The arcuate shapes cause the pawls 346, 348 to be biased against the gear 314.

At least one elongated shape memory element 350 is connected between the cage 344 of the moveable pawl assembly 342 and at least one member 352 fixed with respect to the cage 344, such that the changeable length of the shape memory element 350 decreasing from an uncharged length to a charged length causes linear movement of the moveable pawl assembly 342 with respect to the gear 314. Preferably, the shape memory element 350 extends between opposing first and second ends secured to members 352, 354 fixed with respect to the cage 344 (e.g., fixed internal portions of the housing of the fluid delivery device), and the cage 344 is secured to the shape memory element 350 between the first and the second ends and divides the shape memory element 350 into a first portion 356 extending between the first end and the cage 344 and a second portion 358 extending between the cage 344 and the second end. The first and the second portions 356, 358 of the shape memory element 350 can be individually and alternatively charged to cause reciprocating linear motion of the cage 344.

It should be understood that the shape memory element 350 can comprise a one-way or a two-way shape memory material, as desired. In addition, the shape memory element 350 can include parallel portions similar to the shape memory element 320 of FIG. 10, if desired. The first and the second pawls 346, 348, the cage 344 and the shape memory element 350 can be provides as a single unitary piece of shape memory material, or can be assembled from separate pieces made from different materials.

Figure 11A:
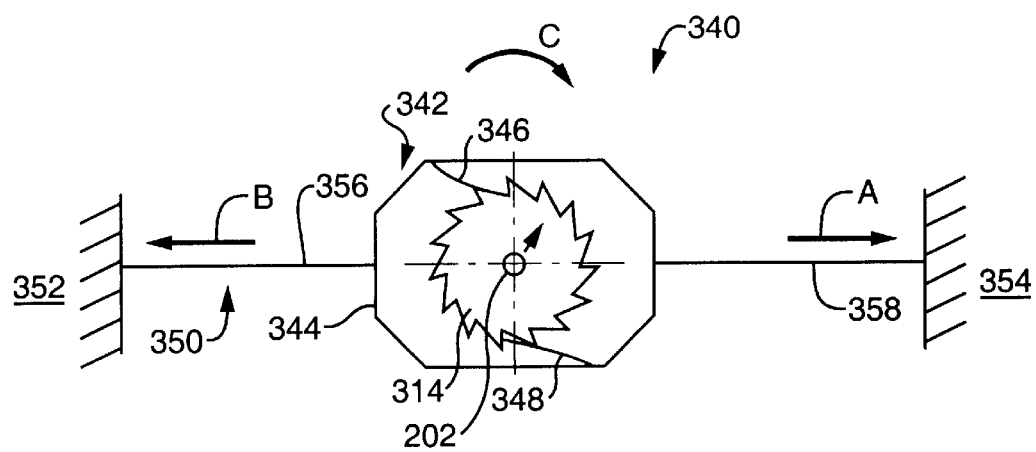
FIGS. 11a through 11e are schematic end elevation views illustrating operation of still another exemplary embodiment of a dispenser constructed in accordance with the present invention for turning the lead screw of the fluid delivery device of FIG. 1.
Figure 11B:
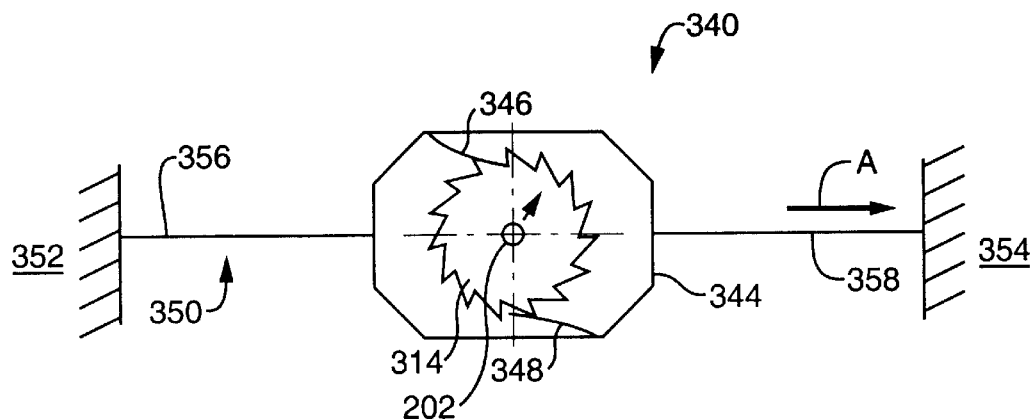
Figure 11C:
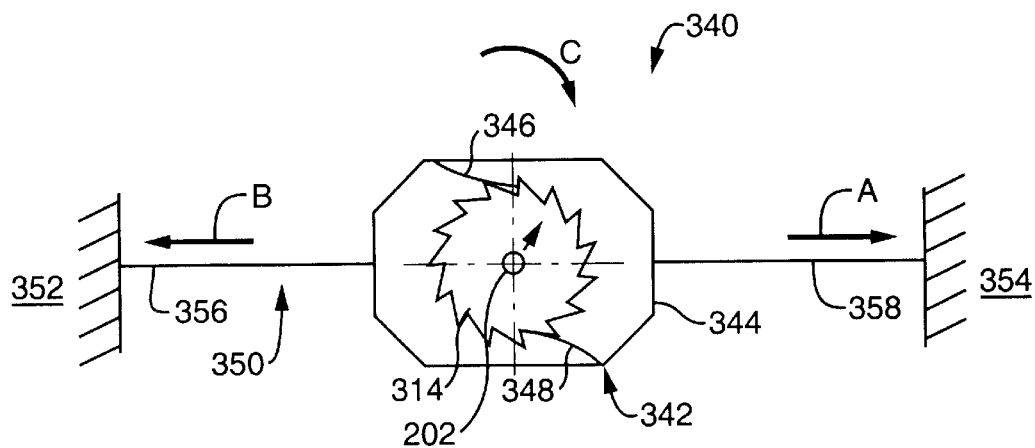
Figure 11D:
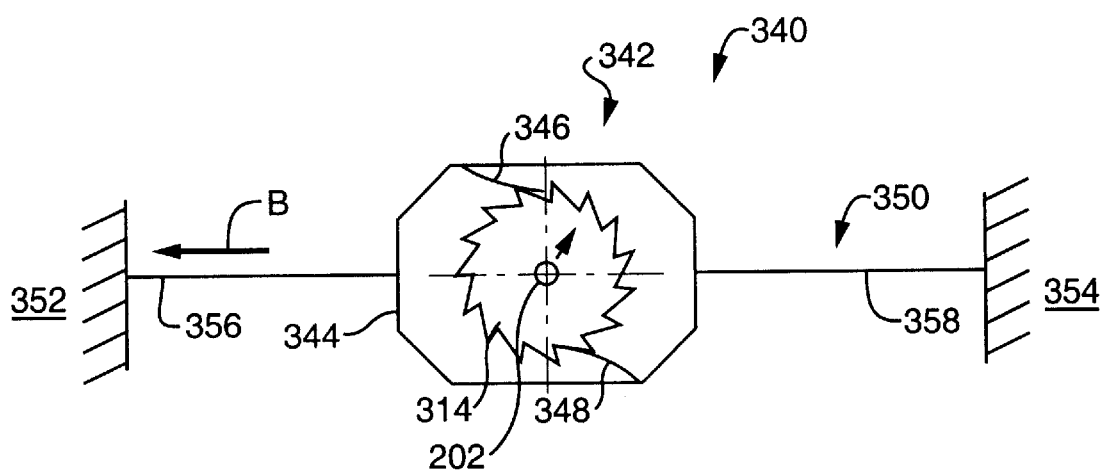
Figure 11E:
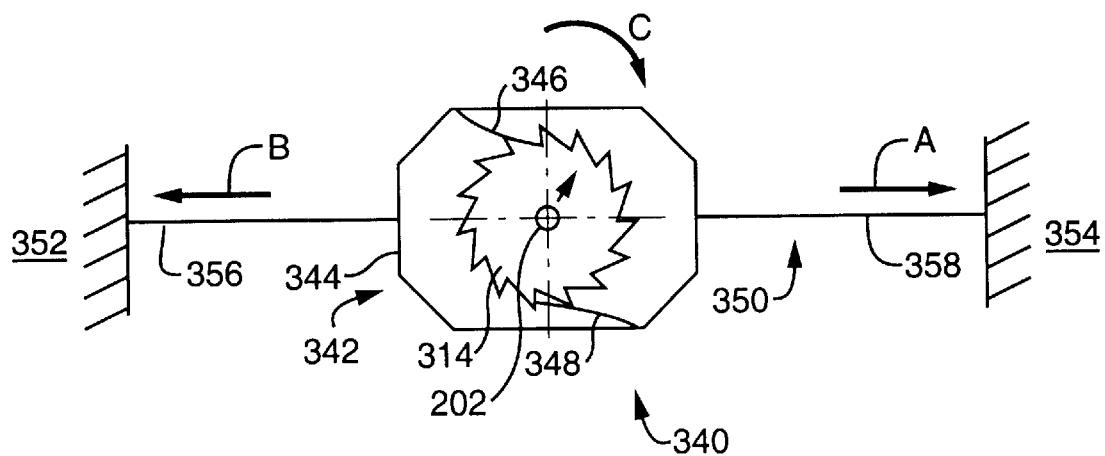

FIGS. 11a through 11e illustrated operation of the dispenser 340. In FIG. 11a, no charge is applied to the shape memory element 350, while in FIGS. 11b and 11c a charge is applied to the second portion 358 of the shape memory element 350 to linearly move the cage 344 in the first linear direction "A". As shown, the first pawl 346 rotates the gear 314 in the first rotational direction "C" during linear movement of the cage 344 in the first linear direction "A", but by not more than a single pitch of the gear 314. In FIGS. 11d and 11e the charge is removed from the second portion 358 of the shape memory element 350 and a charge is applied to the first portion 356 of the shape memory element 350 to linearly move the cage 344 in the second linear direction "B". As shown, the second pawl 348 rotates the gear 314 in the first rotational direction "C" during linear movement of the cage 344 in the second linear direction "B", but by not more than a single pitch of the gear 314. Preferably, the first pawl 346 and the second pawl 348 are offset by a single tooth pitch of the gear 314. In total, therefore, the full linear motion of the cage 344 has advanced the gear 314 by only a single pitch. The biased and arcuate first and second pawls 346, 348 also prevent rotation of the gear 314 in a direction opposite the first rotational direction "C".

Figure 12:
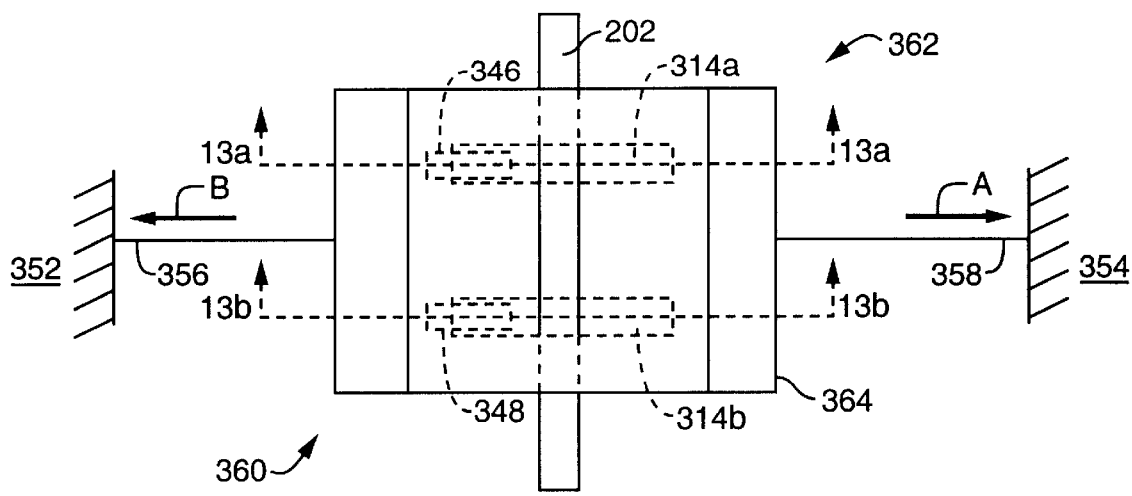
FIG. 12 is a top plan view of a further exemplary embodiment of a dispenser constructed in accordance with the present invention for turning the lead screw of the fluid delivery device of FIG. 1.
Figure 13A:
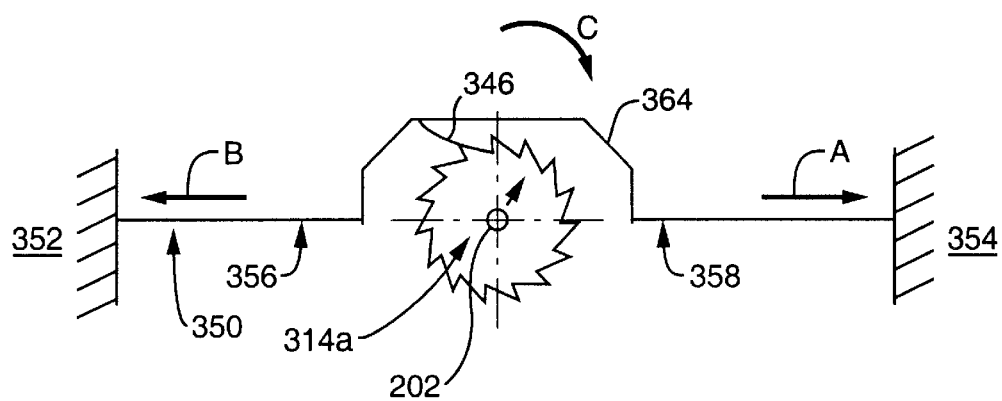
FIG. 13a is a smaller sectional view of the dispenser and the lead screw taken along line 13a—13a of FIG. 12.
Figure 13B:
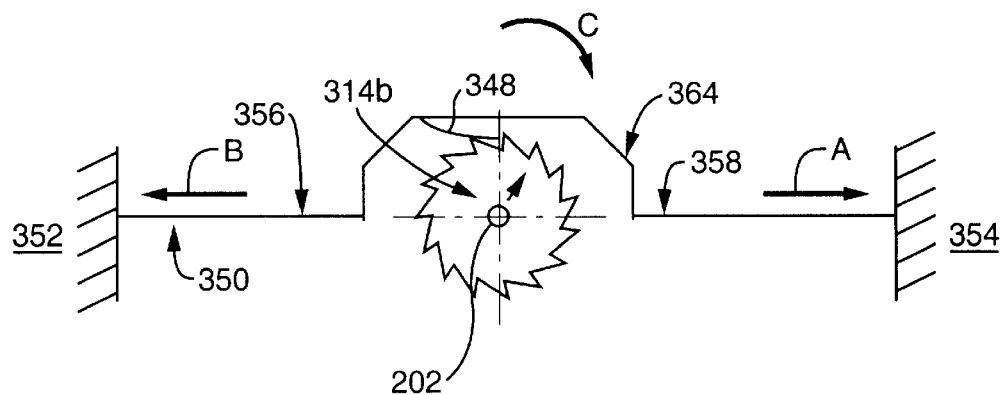
FIG. 13b is a smaller sectional view of the dispenser and the lead screw taken along line 13b—13b of FIG. 12.

A further exemplary embodiment of a dispenser 360 constructed in accordance with the present invention is shown in FIGS. 12, 13a and 13b. The dispenser 360 also produces very small rotations of the lead screw 202 and includes first and second gears 314a, 314b coaxially secured to the lead screw 202 for rotation therewith.

The dispenser 360 also includes a moveable pawl assembly 362 including a cage 364 movable in opposing first and second linear directions adjacent the gears 314a, 314b. A first pawl 346 extends from the cage 364 and is biased against teeth of the first gear 314a, and the first pawl 346 and the teeth of the first gear 314a are shaped and oriented such that the first pawl 346 rotates the first gear 314a in the first rotational direction during linear movement of the cage 364 in the first linear direction, but causes no rotation of the first gear 314a during linear movement of the cage 364 in the second linear direction. In addition, the first pawl 346 prevents rotation of the first gear 314a in an opposite second rotational direction. A second pawl 348 extends from the cage 364 and is biased against teeth of the second gear 314b, and the second pawl 348 and the teeth of the second gear are shaped and oriented such that the second pawl 348 rotates the second gear 314b in the first rotational direction during linear movement of the cage 364 in the first linear direction, but causes no rotation of the second gear 314b during linear movement of the cage 364 in the second linear direction. In addition, the second pawl 348 prevents rotation of the second gear 314b in the opposite second rotational direction.

According to one exemplary embodiment, the first and the second pawls 346, 348 have the same length, and the first and the second gears 314a, 314b are identical but are out of phase on the lead screw 202 by a single tooth pitch. Again, this arrangement provides very small increments of lead screw rotation 202 without requiring additional elements, such as reducing gears connected between the lead screw 202 and the pawl assembly 362.

At least one elongated shape memory element 350 is connected between the cage 364 of the moveable pawl assembly 362 and at least one member 252 fixed with respect to the cage 364, such that the changeable length of the shape memory element decreasing from an uncharged length to a charged length causes linear movement of the moveable pawl assembly 362 with respect to the gears 316a, 316b. Preferably, the shape memory element 350 extends between opposing first and second ends secured to members 352, 354 fixed with respect to the cage 364 (e.g., fixed internal portions of the housing of the fluid delivery device), and the cage 364 is secured to the shape memory element 350 between the first and the second ends and divides the shape memory element 350 into a first portion 352 extending between the first end and the cage 364 and a second portion 354 extending between the cage 364 and the second end. The first and the second portions 352, 354 of the shape memory element 350 can be individually and alternatively charged to cause reciprocating linear motion of the cage 364.

It should be understood that the shape memory element 350 can comprise a one-way or a two-way shape memory material, as desired. In addition, the shape memory element can include parallel portions similar to the shape memory element 320 of FIG. 10, if desired. The first and the second pawls 346, 348, the cage 364 and the shape memory element 350 can be provides as a single unitary piece of shape memory material, or can be assembles from separate pieces made from different materials.

Figure 14:
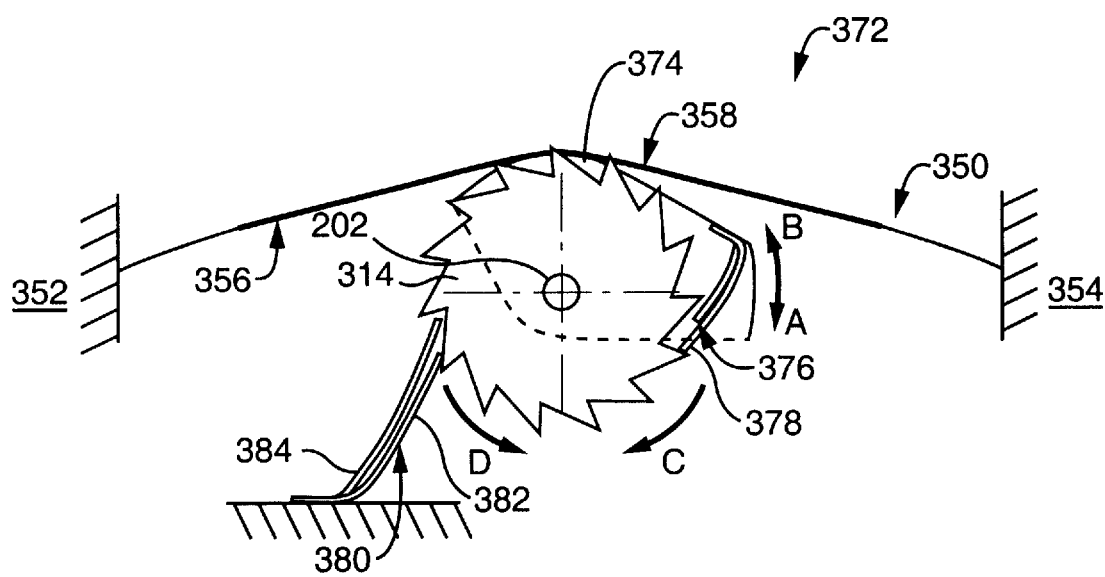
FIG. 14 is an end elevation view of yet another exemplary embodiment of a dispenser constructed in accordance with the present invention for turning the lead screw of the fluid delivery device of FIG. 1.

Still another exemplary embodiment of a dispenser 370 constructed in accordance with the present invention is shown in FIG. 14. The dispenser 370 includes a gear 314 secured to the lead screw 202 for rotation therewith, and a moveable pawl assembly 372 having a cam 374 pivotally mounted coaxially on the lead screw 202 adjacent the gear 314 for pivotal movement in a first pivotal direction "A" and a second pivotal direction "B" about the lead screw 202.

A first pawl 376 is secured to the cam 374 and extends towards the gear 314, and the first pawl 376 and the teeth of the gear 314 are shaped and oriented such that the first pawl 376 rotates the gear 314 in a first rotational direction "C" during pivotal movement of the cam 374 in the first pivotal direction "A", but causes no rotation of the gear 314 during pivotal movement of the cam 374 in the second pivotal direction "B". A second pawl 378 is secured to the cam 374 and extends towards the teeth of the gear 314, wherein the second pawl 378 and the teeth of the gear 314 are shaped and oriented such that the second pawl 378 rotates the gear 314 in the first rotational direction "C" during pivotal movement of the cam 374 in the first pivotal direction "A", but causes no rotation of the gear during pivotal movement of the cam 374 in the second pivotal direction "B". The first and second pawls 376, 378 have different lengths such that pivotal movement of the cam 374 in the first pivotal direction "A" produces less than a tooth pitch of gear 314 advancement. In particular, a difference in the lengths of the first and the second pawls 376, 378 are less than a single tooth pitch of the gear 314.

At least one elongated shape memory element 350 is connected between the cam 374 of the moveable pawl assembly 372 and at least one member 352 fixed with respect to the cam 374, such that the changeable length of the shape memory element 350 decreasing from an uncharged length to a charged length causes pivotal movement of the cam 374 with respect to the gear 314. Preferably, the shape memory element 350 extends between opposing first and second ends secured to members 352, 354 fixed with respect to the cam 374 (e.g., fixed internal portions of the housing of the fluid delivery device), and the cam 374 is secured to the shape memory element 350 between the first and the second ends and divides the shape memory element into a first portion 356 extending between the first end and the cam 374 and a second portion 358 extending between the cam 374 and the second end.

The first and the second portions 356, 358 of the shape memory element 350 can be individually and alternatively charged to cause reciprocating pivoting motion of the cam 374 and rotation of the gear 314. In particular, charging the first portion 356 causes pivotal movement of the cam 374 in the first pivotal direction "A", while charging the second portion 358 causes pivotal movement of the cam 374 in the second pivotal direction "B".

It should be understood that the shape memory element 350 can comprise a one-way or a two-way shape memory material, as desired. In addition, the shape memory element 350 can include parallel portions similar to the shape memory element 320 of FIG. 10, if desired.

Figure 15:
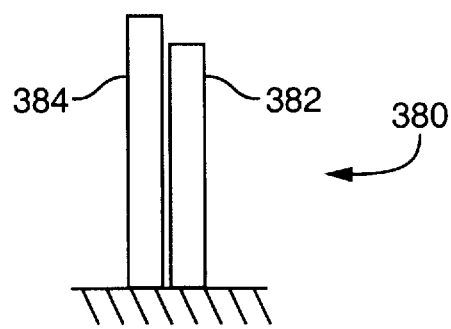
FIG. 15 is a side elevation view of a pawl assembly of the dispenser of FIG. 14.

110 The dispenser 370 of FIG. 14 also includes a fixed pawl assembly 380 for preventing rotation of the gear 314 in a second rotation direction "D" opposite the first rotation direction "C". As also shown in FIG. 15, the fixed pawl assembly 380 includes at least two fixed pawls 382, 384 having different lengths. In the embodiment shown, the pawls 382, 384 are provided with an elongated, arcuate shape. A difference in the lengths of the pawls 382, 384 of the fixed pawl assembly 380 are preferably less than a single tooth pitch of the gear 314, such that the fixed pawl assembly 380 prevents rotation of the gear 314 by less than a single tooth pitch. More than two pawls can be employed in the fixed pawl assembly 380.

Figure 16:
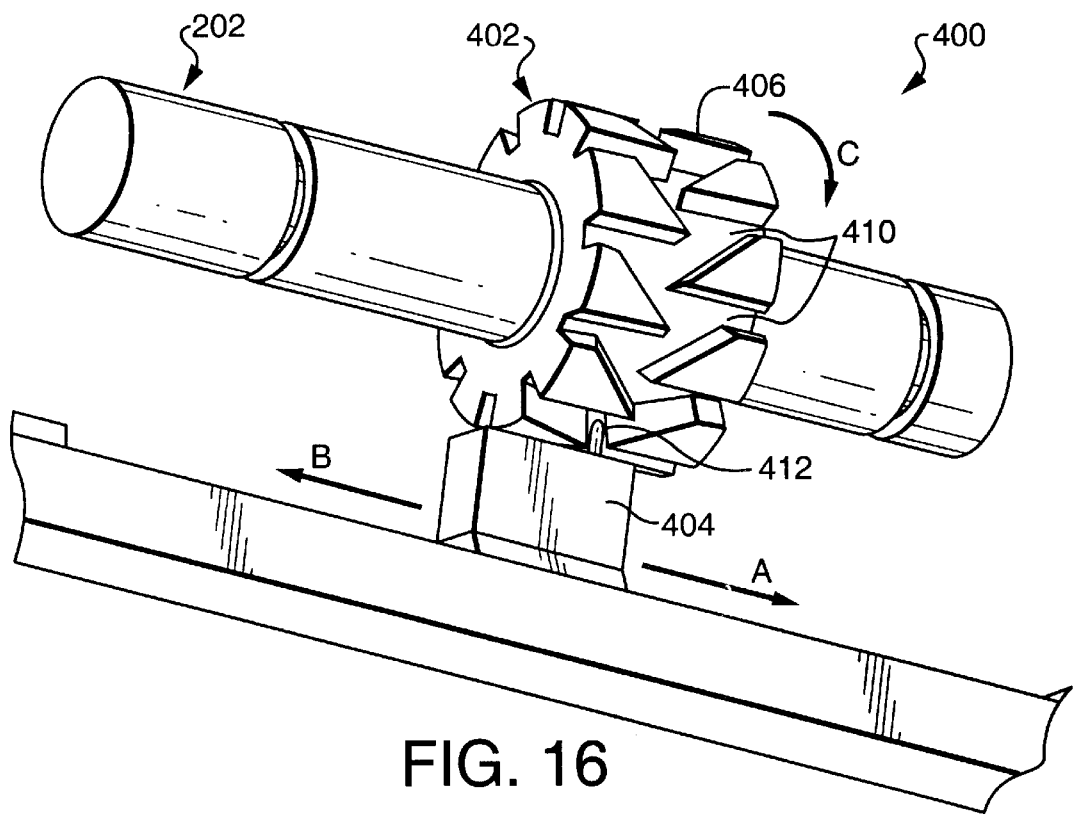
FIG. 16 is a perspective view of an exemplary embodiment of a lead screw of the fluid delivery device of FIG. 1, and an additional exemplary embodiment of a dispenser including a barrel cam constructed in accordance with the present invention for turning the lead screw.

Still another exemplary embodiment of a dispenser 400 constructed in accordance with the present invention is shown in FIG. 16. The dispenser 400 includes a barrel cam 402 coaxially secured to the lead screw 202 for rotation therewith, and a slide 404 that is linearly reciprocatable in opposing first and second linear directions "A" and "B" for causing rotation of the barrel cam 402 in a first rotational direction "C".

Figure 17:
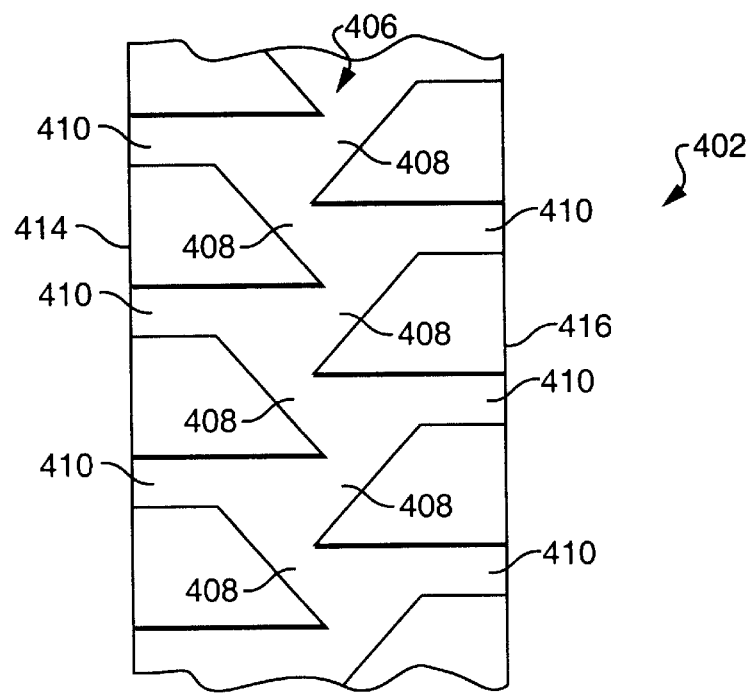
FIG. 17 is an enlarged and "unrolled" plan view of a portion of the barrel cam of the dispenser of FIG. 16.

112 As also shown in FIG. 17, the barrel cam 402 includes a continuous circumferential groove 406 with helical segments 408 having orientations extending in the first rotational direction "C" and successively alternating between opposing first and second ends 414, 416 of the barrel cam 402. As shown in FIG. 16, the slide 404 is linearly movable in opposing first and second linear directions "A" and "B"

parallel with the lead screw 202 and adjacent the barrel cam 402. The slide 404 includes a finger 412 extending from the slide 404 and into the circumferential groove 406 of the barrel cam 402. When the finger 412 extends into one of the helical segments 408, linear movement of the slide 404 in either linear direction "A" or "B" causes rotation of the barrel cam 402 and the lead screw 202 in the first rotational direction "C".

In the exemplary embodiment of FIGS. 16 and 17, the groove 406 of the barrel cam 402 also includes axial segments 410 extending axially, with respect to the barrel cam 402 and the lead screw 202, from each of junctures between the successive helical segments 408 towards the ends 414, 416 of the barrel cam 402. When the finger 412 extends into one of the axial segments 410, linear movement of the slide 404 causes no rotation of the barrel cam 402 and the lead screw 202. The combination of helical and axial segments 408, 410 can be used to control the amount of rotational motion of the lead screw 202 produced from the linear motion of the slide 404. In particular, the embodiment of FIGS. 16 and 17 converts the reciprocating linear motion of the slide 404 into intermittent rotary motion of the barrel cam 402 and the lead screw 202 in the first rotary direction "C".

Although not shown, one or more shape memory elements can be used to cause linear movement of the slide 404 in the linear directions "A" and "B". The shape memory element can comprise a one-way or a two-way shape memory material, as desired. In addition, the shape memory element can include parallel portions similar to the shape memory element 320 of FIG. 10, if desired.

Figure 18:
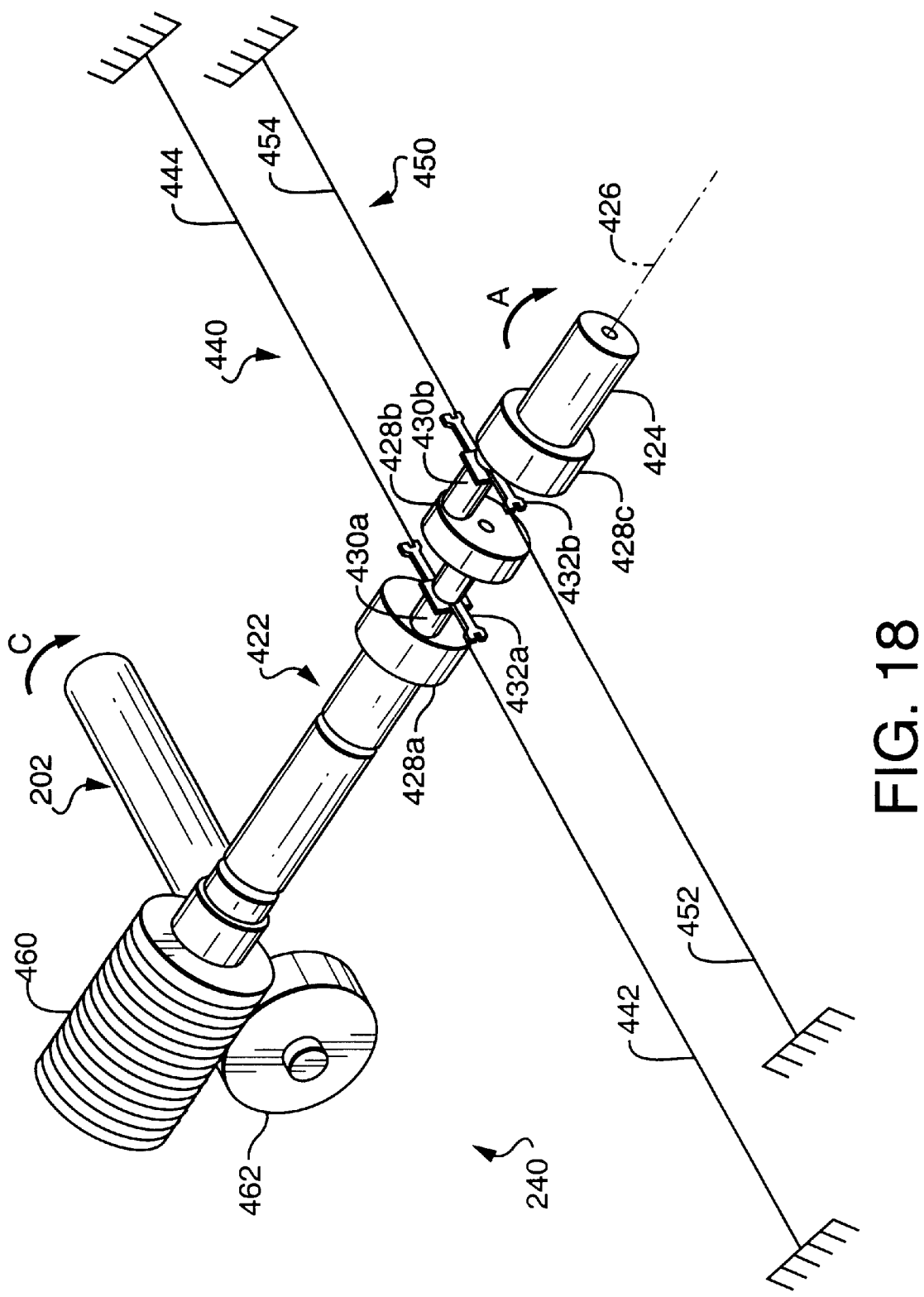
FIG. 18 is a perspective view of an exemplary embodiment of a lead screw of the fluid delivery device of FIG. 1, and a further exemplary embodiment of a dispenser constructed in accordance with the present invention for turning the lead screw.

Another exemplary embodiment of a dispenser 420 constructed in accordance with the present invention is shown in FIG. 18. The dispenser 420 has a crankshaft 422 operatively connected to the lead screw 202 such that rotation of the crankshaft 422 in a first rotational direction "A" of the crankshaft 422 causes rotation of the lead screw 202 in a first rotational direction "C" of the lead screw 202. The crankshaft 422 includes a main shaft 424 rotatable about a longitudinal axis 426, at least one counter weight 428 secured to the main shaft for rotation therewith, and at least one crank pin 430. The crank pin 430 is secured to the main shaft 424 through the counter weight 428 and has a longitudinal axis parallel to but radially offset from the longitudinal axis 426 of the main shaft 424.

Figure 19:
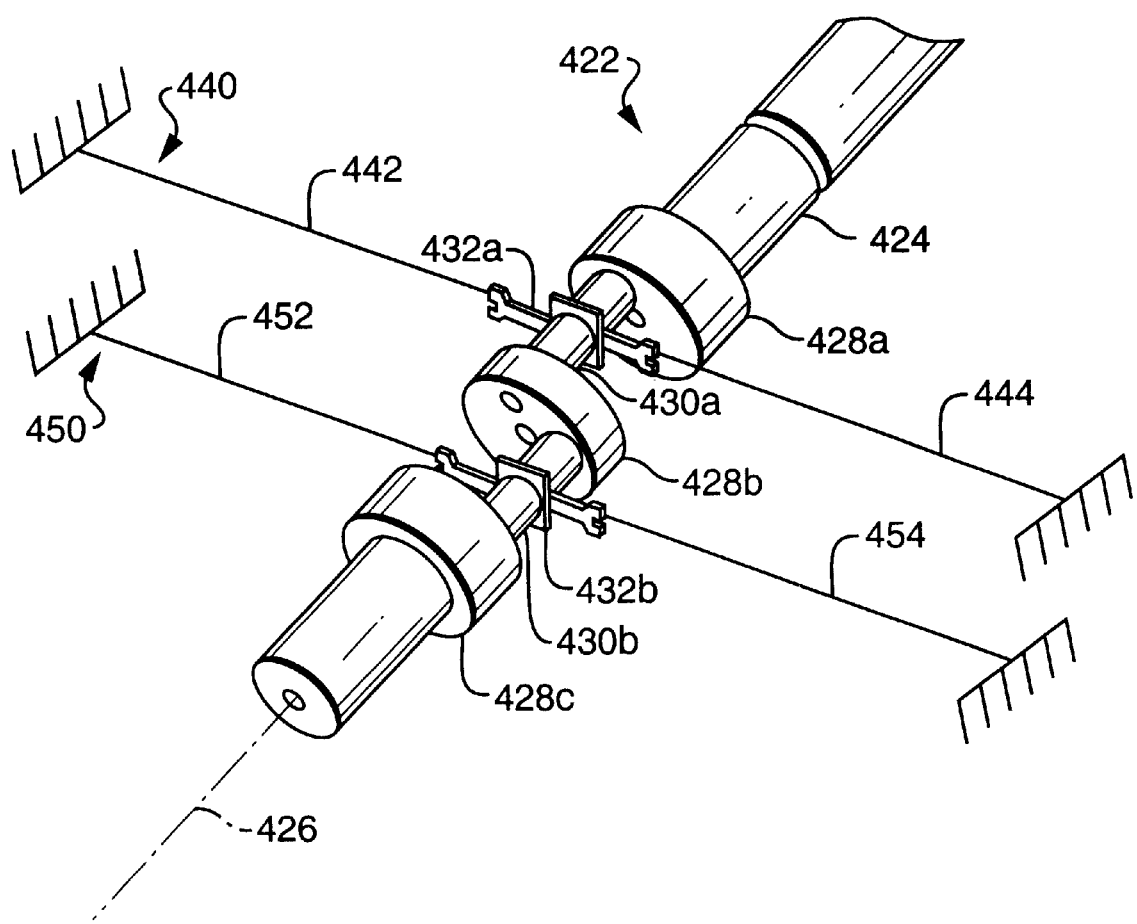
FIG. 19 is an enlarged perspective view of a portion of the dispenser of FIG. 18.

As also shown in FIG. 19, the crankshaft 422 preferably includes first and second crank pins 430a, 430b secured to the main shaft 424 through three counter weights 428a, 428b, 428c. The longitudinal axis of each crank pin 430a, 430b is parallel to but radially offset from the longitudinal axis 428 of the main shaft 424 and parallel to but radially offset from the longitudinal axis of the other crank pin. In the exemplary embodiment shown, the first and the second crank pins 430a, 430b are offset (i.e., out of phase) by ninety degrees.

A catch 432a, 432b is mounted for rotation on each of the crank pins 430a, 430b. A first shape memory element 440 extends between two members fixed with respect to the crankshaft 422 and is secured to the catch 432a of the first crank pin 430a, which divides the first shape memory element 440 into a first portion 442 and a second portion 444. A second shape memory element 450 extends between two members fixed with respect to the crankshaft 422 and is secured to the catch 432b of the second crank pin 430b, which divides the second shape memory element 450 into a first portion 452 and a second portion 454. The shape memory elements 440, 450 can each comprise a one-way or a two-way shape memory material, as desired. In addition, the shape memory elements 440, 450 can include parallel portions similar to the shape memory element 320 of FIG. 10, if desired.

During operation of the dispenser 420, the portions of the shaped memory elements 440, 450 are successively charged in the following order to cause rotation of the crankshaft 422: 1 the first portion 442 of the first shape memory element 440; 2 the second portion 454 of the second shape memory element 450; 3 the second portion 444 of the first shape memory element 440; and 4 the first portion 452 of the second shape memory element 450.

In the exemplary embodiment of FIG. 18, the crankshaft 422 is oriented at a right angle with respect to the lead screw 202 and is operatively connected to the lead screw 202 through a pair of cross-helical gears 460, 462 (i.e., worm gears). The cross-helical gears 460, 462 can be configured to convert ninety degree angular displacements of the crankshaft 422 in relatively small angular displacements of the lead screw 202 (e.g., six degrees), and thus can generate very precise motions of the lead screw 202.

As illustrated by the above described exemplary embodiments, the present invention generally provides a device for delivering fluid, such as insulin for example, to a patient. The device includes an exit port assembly, a syringe-like reservoir including a side wall extending towards an outlet connected to the exit port assembly. A threaded lead screw is received in the reservoir and a plunger has an outer periphery linearly slideable along the side wall of the reservoir and an inner periphery threadedly received on the lead screw. The plunger is non-rotatable with respect to the side wall such that rotating the lead screw causes the plunger to advance within the reservoir and force fluid through the outlet. The device also includes a dispenser having a shape memory element, and a changeable length of the shape memory element decreasing from an uncharged length to a charged length is used to cause rotation of the lead screw.

It should be understood that in each of the above described embodiments, a spring (compression or other type), can be used in place of one of the portions of shape memory elements for actually turning the lead screw and advancing the plunger. The shape memory element in such a case is then used just to reset the spring and place the spring in its energized state (e.g., compressing a helical compression spring), and the spring force is used to provide the force to cause infusion of fluid. Co-pending U.S. patent application Ser. No. 10/128,203, entitled DISPENSER FOR PATIENT INFUSION DEVICE, which was filed on the same day as the present application and is assigned to the assignee of the present application, specifically discloses and claims embodiments of such spring actuation elements, and has been incorporated herein by reference.

In any event, it should be understood that the embodiments described herein are merely exemplary and that a person skilled in the art may make variations and modifications to the embodiments described without departing from the spirit and scope of the present invention. All such equivalent variations and modifications are intended to be included within the scope of this invention as defined by the appended claims.

What is claimed is:

1. A device for delivering fluid to a patient, comprising:
   an exit port assembly;
   a reservoir including a side wall extending towards an outlet connected to the exit port assembly;

a threaded lead screw received at least partly in the reservoir and extending towards the outlet;

a plunger secured to the lead screw and having an outer periphery linearly slideable along the side wall of the reservoir, wherein the plunger and the lead screw are operatively arranged such that rotating the lead screw in a first rotational direction causes the plunger to slide along the side wall towards the outlet of the reservoir;

a dispenser including, a gear secured to the lead screw and including radially extending teeth, a moveable pawl positioned for contacting the teeth of the gear during reciprocating linear movement of the moveable pawl adjacent the gear in first and second opposing linear directions, wherein the moveable pawl and the teeth are shaped such that linear movement of the moveable pawl past the gear in the first linear direction causes rotation of the gear in the first rotational direction while linear movement of the moveable pawl past the gear in the second linear direction causes no rotation of the gear, an elongated shape memory element having a changeable length decreasing from an uncharged length to a charged length when at least one charge is applied to the shape memory element, the shape memory element connected between the moveable pawl and at least one fixed member such that the changeable length of the shape memory element decreasing from an uncharged length to a charged length causes linear movement of the moveable pawl past the gear in one of the first and the second linear directions.

2. A device according to claim 1, wherein the shape memory element extends between two fixed members and the moveable pawl is secured to the shape memory element between the two fixed members.

3. A device according to claim 1, wherein the shape memory element comprises two-way shape memory material.

4. A device according to claim 1, wherein the shape memory element comprises one-way shape memory material.

5. A device according to claim 1, wherein the shape memory element comprises a wire.

6. A device according to claim 1, wherein the shape memory element is made of a nickel and titanium alloy.

7. A device according to claim 1, wherein:

the shape memory element extends between opposing first and second ends secured to fixed members;

the moveable pawl is secured to the shape memory element between the first and the second ends and divides the shape memory element into a first portion extending between the first end and the moveable pawl and a second portion extending between the moveable pawl and the second end; and wherein three separate electrical wires are secured respectively to the first end of the shape memory element, the second end of the shape memory element, and the moveable pawl so that the first and the second portions of the shape memory element can be individually charged.

8. A device according to claim 1, wherein:

the shape memory element extends between opposing first and second ends secured to fixed members;

the moveable pawl is secured to the shape memory element between the first and the second ends; and the shape memory element includes a first set of at least two elongated parallel portions extending between the first end and the moveable pawl, and a second set of at least two elongated parallel portions extending between the moveable pawl and the second end.

9. A device according to claim 8, wherein three separate electrical wires are secured respectively to the first end of the shape memory element, the second end of the shape memory element, and the moveable pawl so that the first and the second sets of parallel portions can be individually charged.

10. A device according to claim 1, wherein the plunger is threadedly received on the lead screw and prevented from rotating with respect to the side wall of the reservoir.

11. A device according to claim 10, wherein a portion of the side wall of the reservoir and a portion of the plunger have mating non-circular cross-sections.

12. A device according to claim 1, further comprising a fixed pawl preventing rotation of the gear in a second rotational direction opposite the first rotational direction.

13. A device according to claim 1, wherein the moveable pawl and the shape memory element comprise a single, unitary piece.

14. A device according to claim 1, further comprising:

a local processor connected to ends of the shape memory element and programmed to provide charges to the shape memory element based upon flow instructions;

a wireless receiver connected to the local processor for receiving flow instructions from a separate, remote control device and delivering the flow instructions to the local processor; and a housing containing the reservoir, the exit port assembly, the dispenser, the local processor and the wireless receiver, wherein the housing is free of user input components for providing flow instructions to the local processor.

15. A system including a fluid delivery device according to claim 14, and further comprising a remote control device separate from the fluid delivery device and including:

a remote processor;

user interface components connected to the remote processor for allowing a user to provide flow instructions to the remote processor; and a transmitter connected to the remote processor for transmitting the flow instructions to the receiver of the fluid delivery device.

16. A device according to claim 1, wherein the reservoir contains a therapeutic fluid.

17. A device according to claim 16, wherein the therapeutic fluid is insulin.

18. A device according to claim 1, wherein the exit port assembly includes a transcutaneous patient access tool.

19. A device according to claim 18, wherein the transcutaneous patient access tool comprises a needle.

20. A device according to claim 1, further comprising a local processor connected to ends of the shape memory element and programmed to provide charges to the shape memory element based upon flow instructions.

21. A device according to claim 20, further comprising a power supply connected to the local processor.

22. A device according to claim 1, further comprising a fixed pawl assembly preventing rotation of the gear in a second rotational direction opposite the first rotational direction, wherein the fixed pawl assembly includes a pawl and a spring biasing the pawl against the gear.

23. A device according to claim 1, further comprising a fixed pawl assembly preventing rotation of the gear in a second rotational direction opposite the first rotational direction, wherein the fixed pawl assembly includes at least two fixed pawls having different lengths.

24. A device for delivering fluid to a patient, comprising:
an exit port assembly;
a reservoir including a side wall extending towards an outlet connected to the exit port assembly;
a threaded lead screw received at least partly in the reservoir and extending towards the outlet;
a plunger secured to the lead screw and having an outer periphery linearly slideable along the side wall of the reservoir, wherein the plunger and the lead screw are operatively arranged such that rotating the lead screw in a first rotational direction causes the plunger to slide along the side wall towards the outlet of the reservoir;
a gear secured to the lead screw and including radially extending teeth;
a moveable pawl assembly including,
a cage coaxially arranged with respect to the lead screw about the gear, the cage linearly movable in opposing first and second linear directions,
a first pawl extending from the cage and biased against the teeth of the gear, wherein the first pawl and the teeth are shaped and oriented such that the first pawl rotates the gear in the first rotational direction during linear movement of the cage in the first linear direction but causes no rotation of the gear during linear movement of the cage in the second linear direction and wherein the first pawl prevents rotation of the gear in an opposite second rotational direction, and
a second pawl extending from the cage and biased against the teeth of the gear, wherein the second pawl and the teeth are shaped and oriented such that the second pawl rotates the gear in the first rotational direction during linear movement of the cage in the second linear direction but causes no rotation of the gear during linear movement of the cage in the first linear direction and wherein the second pawl prevents rotation of the gear in the opposite second rotational direction.

25. A device according to claim 24, further comprising at least one elongated shape memory element having a changeable length decreasing from an uncharged length to a charged length when at least one charge is applied to the shape memory element, the shape memory element connected between the cage of the moveable pawl assembly and at least one member fixed with respect to the cage, such that the changeable length of the shape memory element decreasing from an uncharged length to a charged length causes linear movement of the moveable pawl assembly with respect to the gear.

26. A device according to claim 25, wherein:
the shape memory element extends between opposing first and second ends secured to members fixed with respect to the cage;
the cage is secured to the shape memory element between the first and the second ends and divides the shape memory element into a first portion extending between the first end and the cage and a second portion extending between the cage and the second end; and
wherein the first and the second portions of the shape memory element can be individually charged.

27. A device according to claim 25, wherein:
the shape memory element extends between opposing first and second ends secured to fixed members;
the cage is secured to the shape memory element between the first and the second ends;

the shape memory element includes a first set of at least two elongated parallel portions extending between the first end and the cage, and a second set of at least two elongated parallel portions extending between the cage and the second end; and
wherein the first and the second sets of the shape memory element can be individually charged.

28. A device according to claim 25, wherein the shape memory element comprises two-way shape memory material.

29. A device according to claim 25, wherein the shape memory element comprises one-way shape memory material.

30. A device according to claim 25, wherein the shape memory element comprises a wire.

31. A device according to claim 25, wherein the shape memory element is made of a nickel and titanium alloy.

32. A device according to claim 24, wherein the plunger is threadedly received on the lead screw and prevented from rotating with respect to the side wall of the reservoir.

33. A device according to claim 32, wherein a portion of the side wall of the reservoir and a portion of the plunger have mating non-circular cross-sections.

34. A device according to claim 24, wherein the plunger includes a resiliently flexible tip providing a substantially fluid tight seal between the plunger and the side wall of the reservoir.

35. A device according to claim 24, wherein the first and the second pawls are resiliently flexible.

36. A device according to claim 24, wherein the first and the second pawls have arcuate profiles.

37. A device according to claim 24, wherein the first pawl and the second pawl are offset with respect to a tooth pitch of the gear.

38. A device according to claim 24, wherein the first and the second pawls and the cage comprise a single, unitary piece.

39. A device according to claim 25, wherein the cage and the shape memory element comprise a single, unitary piece.

40. A device according to claim 25, further comprising:
a local processor connected to ends of the shape memory element and programmed to provide charges to the shape memory element based upon flow instructions;
a wireless receiver connected to the local processor for receiving flow instructions from a separate, remote control device and delivering the flow instructions to the local processor; and
a housing containing the reservoir, the exit port assembly, the dispenser, the local processor and the wireless receiver, wherein the housing is free of user input components for providing flow instructions to the local processor.

41. A system including a fluid delivery device according to claim 40, and further comprising a remote control device separate from the fluid delivery device and including:
a remote processor;
user interface components connected to the remote processor for allowing a user to provide flow instructions to the remote processor; and
a transmitter connected to the remote processor for transmitting the flow instructions to the receiver of the fluid delivery device.

42. A device according to claim 40, further comprising a power supply connected to the local processor.

43. A device according to claim 24, wherein the reservoir contains a therapeutic fluid.

44. A device according to claim 43, wherein the therapeutic fluid is insulin.

45. A device according to claim 24, wherein the exit port assembly includes a transcutaneous patient access tool.

46. A device according to claim 45, wherein the transcutaneous patient access tool comprises a needle.

47. A device for delivering fluid to a patient, comprising:
an exit port assembly;
a reservoir including a side wall extending towards an outlet connected to the exit port assembly;
a threaded lead screw received at least partly in the reservoir and extending towards the outlet;
a plunger secured to the lead screw and having an outer periphery linearly slideable along the side wall of the reservoir, wherein the plunger and the lead screw are operatively arranged such that rotating the lead screw in a first rotational direction causes the plunger to slide along the side wall towards the outlet of the reservoir;
a first gear secured to the lead screw and including radially extending teeth;
a second gear secured to the lead screw and including radially extending teeth, wherein the second gear is out of phase with the first gear;
a moveable pawl assembly including,
  a cage movable in opposing first and second linear directions adjacent the gears,
  a first pawl extending from the cage and biased against the teeth of the first gear, wherein the first pawl and the teeth of the first gear are shaped and oriented such that the first pawl rotates the first gear in the first rotational direction during linear movement of the cage in the first linear direction but causes no rotation of the first gear during linear movement of the cage in the second linear direction, and wherein the first pawl prevents rotation of the first gear in an opposite second rotational direction, and
  a second pawl extending from the cage and biased against the teeth of the second gear, wherein the second pawl and the teeth of the second gear are shaped and oriented such that the second pawl rotates the second gear in the first rotational direction during linear movement of the cage in the first linear direction but causes no rotation of the second gear during linear movement of the cage in the second linear direction, and wherein the second pawl prevents rotation of the second gear in the opposite second rotational direction.

48. A device according to claim 47, further comprising at least one elongated shape memory element having a changeable length decreasing from an uncharged length to a charged length when at least one charge is applied to the shape memory element, the shape memory element connected between the cage of the moveable pawl assembly and at least one member fixed with respect to the cage, such that the changeable length of the shape memory element decreasing from an uncharged length to a charged length causes linear movement of the moveable pawl assembly with respect to the gear.

49. A device according to claim 48, wherein:
the shape memory element extends between opposing first and second ends secured to members fixed with respect to the cage;
the cage is secured to the shape memory element between the first and the second ends and divides the shape memory element into a first portion extending between the first end and the cage and a second portion extending between the cage and the second end; and
wherein the first and the second portions of the shape memory element can be individually charged.

50. A device according to claim 48, wherein:
the shape memory element extends between opposing first and second ends secured to fixed members;
the cage is secured to the shape memory element between the first and the second ends;
the shape memory element includes a first set of at least two elongated parallel portions extending between the first end and the cage, and a second set of at least two elongated parallel portions extending between the cage and the second end; and
wherein the first and the second sets of the shape memory element can be individually charged.

51. A device according to claim 48, wherein the shape memory element comprises two-way shape memory material.

52. A device according to claim 48, wherein the shape memory element comprises one-way shape memory material.

53. A device according to claim 48, wherein the shape memory element comprises a wire.

54. A device according to claim 48, wherein the shape memory element is made of a nickel and titanium alloy.

55. A device according to claim 47, wherein the plunger is threadedly received on the lead screw and prevented from rotating with respect to the side wall of the reservoir.

56. A device according to claim 55, wherein a portion of the side wall of the reservoir and a portion of the plunger have mating non-circular cross-sections.

57. A device according to claim 47, wherein the plunger includes a resiliently flexible tip providing a substantially fluid tight seal between the plunger and the side wall of the reservoir.

58. A device according to claim 47, wherein the first and the second pawls are resiliently flexible.

59. A device according to claim 47, wherein the first and the second pawls have arcuate profiles.

60. A device according to claim 47, wherein the first pawl and the second pawl have a similar length.

61. A device according to claim 47, wherein the first and the second gears are identical and are out of phase by a single tooth pitch.

62. A device according to claim 47, wherein the first and the second pawls and the cage comprise a single, unitary piece.

63. A device according to claim 48, wherein the cage and the shape memory element comprise a single, unitary piece.

64. A device according to claim 48, further comprising:
a local processor connected to ends of the shape memory element and programmed to provide charges to the shape memory element based upon flow instructions;
a wireless receiver connected to the local processor for receiving flow instructions from a separate, remote control device and delivering the flow instructions to the local processor; and
a housing containing the reservoir, the exit port assembly, the dispenser, the local processor and the wireless receiver, wherein the housing is free of user input components for providing flow instructions to the local processor.

65. A system including a fluid delivery device according to claim 64, and further comprising a remote control device separate from the fluid delivery device and including:
a remote processor;
user interface components connected to the remote processor for allowing a user to provide flow instructions to the remote processor; and a transmitter connected to the remote processor for transmitting the flow instructions to the receiver of the fluid delivery device.

66. A device according to claim 64, further comprising a power supply connected to the local processor.

67. A device according to claim 47, wherein the reservoir contains a therapeutic fluid.

68. A device according to claim 67, wherein the therapeutic fluid is insulin.

69. A device according to claim 47, wherein the exit port assembly includes a transcutaneous patient access tool.

70. A device according to claim 69, wherein the transcutaneous patient access tool comprises a needle.

71. A device for delivering fluid to a patient, comprising:
an exit port assembly;
a reservoir including a side wall extending towards an outlet connected to the exit port assembly;
a threaded lead screw received at least partly in the reservoir and extending towards the outlet;
a plunger secured to the lead screw and having an outer periphery linearly slideable along the side wall of the reservoir, wherein the plunger and the lead screw are operatively arranged such that rotating the lead screw in a first rotational direction causes the plunger to slide along the side wall towards the outlet of the reservoir;
a gear coaxially secured to the lead screw for rotation therewith and including radially extending teeth;
a moveable pawl assembly including,
a cam pivotally mounted coaxially on the lead screw adjacent the gear for pivotal movement in opposing first and second pivotal directions about the lead screw;
a first pawl secured to the cam and extending towards the teeth of the gear, wherein the first pawl and the teeth of the gear are shaped and oriented such that the first pawl rotates the gear in the first rotational direction during pivotal movement of the cam in the first pivotal direction, but causes no rotation of the gear during pivotal movement of the cam in the second pivotal direction, and
a second pawl secured to the cam and extending towards the teeth of the gear, wherein the second pawl and the teeth of the gear are shaped and oriented such that the second pawl rotates the gear in the first rotational direction during pivotal movement of the cam in the first pivotal direction, but causes no rotation of the gear during pivotal movement of the cam in the second pivotal direction, and wherein the first and second pawls have different lengths.

72. A device according to claim 71, further comprising at least one elongated shape memory element having a changeable length decreasing from an uncharged length to a charged length when at least one charge is applied to the shape memory element, the shape memory element connected between the cam of the moveable pawl assembly and at least one member fixed with respect to the cam, such that the changeable length of the shape memory element decreasing from an uncharged length to a charged length causes pivotal movement of the cam.

73. A device according to claim 72, wherein:
the shape memory element extends between opposing first and second ends secured to members fixed with respect to the cam;
the cam is secured to the shape memory element between the first and the second ends and divides the shape memory element into a first portion extending between the first end and the cam and a second portion extending between the cam and the second end; and
wherein the first and the second portions of the shape memory element can be individually charged.

74. A device according to claim 72, wherein:
the shape memory element extends between opposing first and second ends secured to fixed members;
the cam is secured to the shape memory element between the first and the second ends;
the shape memory element includes a first set of at least two elongated parallel portions extending between the first end and the cam, and a second set of at least two elongated parallel portions extending between the cam and the second end; and
wherein the first and the second sets of the shape memory element can be individually charged.

75. A device according to claim 72, wherein the shape memory element comprises two-way shape memory material.

76. A device according to claim 72, wherein the shape memory element comprises one-way shape memory material.

77. A device according to claim 72, wherein the shape memory element comprises a wire.

78. A device according to claim 72, wherein the shape memory element is made of a nickel and titanium alloy.

79. A device according to claim 71, wherein the plunger is threadedly received on the lead screw and prevented from rotating with respect to the side wall of the reservoir.

80. A device according to claim 79, wherein a portion of the side wall of the reservoir and a portion of the plunger have mating non-circular cross-sections.

81. A device according to claim 71, wherein the plunger includes a resiliently flexible tip providing a substantially fluid tight seal between the plunger and the side wall of the reservoir.

82. A device according to claim 71, wherein the first and the second pawls are resiliently flexible.

83. A device according to claim 71, wherein the first and the second pawls have arcuate profiles.

84. A device according to claim 71, wherein a difference in the lengths of the first and the second pawls are less than a single tooth pitch of the gear.

85. A device according to claim 72, further comprising:
a local processor connected to ends of the shape memory element and programmed to provide charges to the shape memory element based upon flow instructions;
a wireless receiver connected to the local processor for receiving flow instructions from a separate, remote control device and delivering the flow instructions to the local processor; and
a housing containing the reservoir, the exit port assembly, the dispenser, the local processor and the wireless receiver, wherein the housing is free of user input components for providing flow instructions to the local processor.

86. A system including a fluid delivery device according to claim 85, and further comprising a remote control device separate from the fluid delivery device and including:
a remote processor;
user interface components connected to the remote processor for allowing a user to provide flow instructions to the remote processor; and
a transmitter connected to the remote processor for transmitting the flow instructions to the receiver of the fluid delivery device.

87. A device according to claim 85, further comprising a power supply connected to the local processor.

88. A device according to claim 71, wherein the reservoir contains a therapeutic fluid.

89. A device according to claim 88, wherein the therapeutic fluid is insulin.

90. A device according to claim 71, wherein the exit port assembly includes a transcutaneous patient access tool.

91. A device according to claim 90, wherein the transcutaneous patient access tool comprises a needle.

92. A device according to claim 71, further comprising a fixed pawl assembly preventing rotation of the gear in a second rotational direction opposite the first rotational direction.

93. A device according to claim 92, wherein the fixed pawl assembly includes at least two fixed pawls having different lengths.

94. A device according to claim 93, wherein a difference in the lengths of the pawls of the fixed pawl assembly are less than a single tooth pitch of the gear.

95. A device for delivering fluid to a patient, comprising:
   an exit port assembly;
   a reservoir including a side wall extending towards an outlet connected to the exit port assembly;
   a threaded lead screw received at least partly within the reservoir and extending towards the outlet;
   a plunger secured to the lead screw and having an outer periphery linearly slideable along the side wall of the reservoir, wherein the plunger and the lead screw are operatively arranged such that rotation of the lead screw in a first rotational direction causes the plunger to slide along the side wall towards the outlet of the reservoir; and
   a dispenser including,
      a barrel cam coaxial secured to the lead screw for rotation therewith and including a continuous circumferential groove with helical segments having orientations extending in the first rotational direction and successively alternating between opposing first and second ends of the barrel cam, and
      a slide linearly movable in opposing first and second linear directions parallel with the lead screw and adjacent the gear, the slide including a finger extending from the slide and into the circumferential groove of the barrel cam, whereby, when the finger extends into one of the helical segments, linear movement of the slide causes rotation of the barrel cam and the lead screw in the first rotational direction.

96. A device according to claim 95, wherein the groove of the barrel cam also includes axial segments extending from each of junctures between the successive helical segments and extending axially towards the ends of the barrel cam, whereby, when the finger extends into one of the axial segments, linear movement of the slide causes no rotation of the barrel cam and the lead screw.

97. A device according to claim 95, further comprising at least one elongated shape memory element having a changeable length decreasing from an uncharged length to a charged length when at least one charge is applied to the shape memory element, the shape memory element connected between the slide and a member fixed with respect to the slide such that the changeable length of the shape memory element decreasing from an uncharged length to a charged length causes linear movement of the slide with respect to the barrel cam.

98. A device according to claim 97, wherein the shape memory element comprises a wire.

99. A device according to claim 97, wherein the shape memory element is made of a nickel and titanium alloy.

100. A device according to claim 97, wherein the shape memory element is made of a two-way shape memory material.

101. A device according to claim 97, further comprising:
   a local processor connected to ends of the shape memory element and programmed to provide charges to the shape memory element based upon flow instructions;
   a wireless receiver connected to the local processor for receiving flow instructions from a separate, remote control device and delivering the flow instructions to the local processor; and
   a housing containing the reservoir, the exit port assembly, the dispenser, the local processor and the wireless receiver, wherein the housing is free of user input components for providing flow instructions to the local processor.

102. A device according to claim 101, further comprising a power supply connected to the local processor.

103. A system including a fluid delivery device according to claim 101, and further comprising a remote control device separate from the fluid delivery device and including:
   a remote processor;
   user interface components connected to the remote processor for allowing a user to provide flow instructions to the remote processor; and
   a transmitter connected to the remote processor for transmitting the flow instructions to the receiver of the fluid delivery device.

104. A device according to claim 95, wherein the reservoir contains a therapeutic fluid.

105. A device according to claim 104, wherein the therapeutic fluid is insulin.

106. A device according to claim 95, wherein the exit port assembly includes a transcutaneous patient access tool.

107. A device according to claim 106, wherein the transcutaneous patient access tool comprises a needle.

108. A device for delivering fluid to a patient, comprising:
   an exit port assembly;
   a reservoir including a side wall extending towards an outlet connected to the exit port assembly;
   a threaded lead screw received at least partly in the reservoir and extending towards the outlet;
   a plunger secured to the lead screw and having an outer periphery linearly slideable along the side wall of the reservoir, wherein the plunger and the lead screw are operatively arranged such that rotating the lead screw in a first rotational direction causes the plunger to slide along the side wall towards the outlet of the reservoir;
   a dispenser including,
      a crankshaft operatively connected to the lead screw such that rotation of the crankshaft in a first rotational direction of the crankshaft causes rotation of the lead screw in the first rotational direction of the lead screw, the crankshaft including a main shaft rotatable about a longitudinal axis, at least one counter weight secured to the main shaft for rotation therewith, and at least one crank pin, the crank pin secured to the main shaft through the counter weight and having a longitudinal axis parallel to but radially offset from the longitudinal axis of the main shaft, and at least one elongated shape memory element having a changeable length decreasing from an uncharged length to a charged length when at least one charge is applied to the shape memory element, the shape memory element connected between the crank pin and at least one member fixed with respect to the crankshaft such that the changeable length of the shape memory element decreasing from an uncharged length to a charged length causes rotation of the crankshaft.

109. A device according to claim 108, wherein the shape memory element extends between two members fixed with respect to the crankshaft and the crank pin is secured to the shape memory element between the two fixed members.

110. A device according to claim 108, wherein the shape memory element comprises two-way shape memory material.

111. A device according to claim 108, wherein the shape memory element comprises one-way shape memory material.

112. A device according to claim 108, wherein the shape memory element comprises a wire.

113. A device according to claim 108, wherein the shape memory element is made of a nickel and titanium alloy.

114. A device according to claim 108, wherein a catch is mounted for rotation on the crank pin with respect to the axis of the crank pin and the shape memory element is secured to the crank pin through the catch, extends between two members fixed with respect to the crankshaft, and the catch divides the shape memory element into a first portion extending between a first end of the shape memory element and the catch and a second portion extending between the catch and a second end of the shape memory element.

115. A device according to claim 114, wherein three separate electrical wires are secured respectively to the first end of the shape memory element, the second end of the shape memory element, and the catch so that the first and the second portions of the shape memory element can be individually charged.

116. A device according to claim 1 15, further comprising a local processor connected to the three wires of the shape memory element and programmed to alternatively and successively provided charges to the first and the second portions based upon flow instructions.

117. A device according to claim 108, wherein:
the shape memory element extends between opposing first and second ends secured to fixed members;
a catch is mounted for rotation on the crank pin with respect to the axis of the crank pin and the shape memory element is secured to the crank pin through the catch, and the catch divides the shape memory element into a first portion extending between the first end of the shape memory element and the catch and a second portion extending between the catch and the second end of the shape memory element; and
the shape memory element includes a first set of at least two elongated parallel portions extending between the first end and the catch, and a second set of at least two elongated parallel portions extending between the catch and the second end.

118. A device according to claim 117, wherein three separate electrical wires are secured respectively to the first end of the shape memory element, the second end of the shape memory element, and the catch so that the first and the second sets of parallel portions can be individually charged.

119. A device according to claim 118, further comprising a local processor connected to the three wires of the shape memory element and programmed to alternatively and successively provided charges to the first and the second sets of parallel portions based upon flow instructions.

120. A device according to claim 108, wherein the plunger is threadedly received on the lead screw and prevented from rotating with respect to the side wall of the reservoir.

121. A device according to claim 120, wherein a portion of the side wall of the reservoir and a portion of the plunger have mating non-circular cross-sections.

122. A device according to claim 108, wherein the plunger includes a resiliently flexible tip providing a substantially fluid tight seal between the plunger and the side wall of the reservoir.

123. A device according to claim 108, further comprising:
a local processor connected to ends of the shape memory element and programmed to provide charges to the shape memory element based upon flow instructions;
a wireless receiver connected to the local processor for receiving flow instructions from a separate, remote control device and delivering the flow instructions to the local processor; and
a housing containing the reservoir, the exit port assembly, the dispenser, the local processor and the wireless receiver, wherein the housing is free of user input components for providing flow instructions to the local processor.

124. A system including a fluid delivery device according to claim 123, and further comprising a remote control device separate from the fluid delivery device and including:
a remote processor;
user interface components connected to the remote processor for allowing a user to provide flow instructions to the remote processor; and
a transmitter connected to the remote processor for transmitting the flow instructions to the receiver of the fluid delivery device.

125. A device according to claim 108, wherein the reservoir contains a therapeutic fluid.

126. A device according to claim 125, wherein the therapeutic fluid is insulin.

127. A device according to claim 108, wherein the exit port assembly includes a transcutaneous patient access tool.

128. A device according to claim 127, wherein the transcutaneous patient access tool comprises a needle.

129. A device according to claim 108, further comprising a local processor connected to ends of the shape memory element and programmed to provide charges to the shape memory element based upon flow instructions.

130. A device according to claim 129, further comprising a power supply connected to the local processor.

131. A device according to claim 108, wherein the crankshaft is operatively connected to the lead screw through a pair of cross-helical gears.

132. A device according to claim 108, wherein:
the crank pin of the crankshaft comprises first and second crank pins secured to the main shaft through three counter weights, and wherein the longitudinal axis of each crank pin is parallel to but radially offset from the longitudinal axis of the main shaft and parallel to but radially offset from the longitudinal axis of the other crank pin; and
the shape memory element of the dispenser comprises a first shape memory element secured between the first crank pin and a member fixed with respect to the crankshaft, and a second shape memory element secured between the second crank pin and a member fixed with respect to the crankshaft.

133. A device according to claim 132, wherein a catch is mounted for rotation on each of the crank pins and the shape memory elements are each secured to the crank pins through the catches, extend between two members fixed with respect to the crankshaft, and the catches divide the shape memory elements each into a first portion extending between a first end of the shape memory element and the catch and a second portion extending between the catch and a second end of the shape memory element.

134. A device according to claim 133, wherein each shape memory element includes three separate electrical wires secured respectively to the first end of the shape memory element, the second end of the shape memory element, and the catch so that the first and the second portions of the shape memory element can be individually charged.

135. A device according to claim 134, further comprising a local processor connected to the wires of the shape memory elements and programmed to alternatively and successively provided charges to the portions of the shape memory elements based upon flow instructions.

* * * * *